US012600808B2

(12) United States Patent
Bispinghoff et al.

(10) Patent No.: US 12,600,808 B2
(45) Date of Patent: Apr. 14, 2026

(54) CROSSLINKABLE PREPOLYMERS FOR CHEMICALLY STABLE POLYMER GELS

(71) Applicant: Odne AG, Dübendorf (CH)

(72) Inventors: Mark Bispinghoff, Zurich (CH); Andreas Schmocker, Zurich (CH); Aaron Johnson, Winterthur (CH)

(73) Assignee: Odne AG, Dübendorf (CH)

( * ) Notice: Subject to any disclaimer, the term of this patent is extended or adjusted under 35 U.S.C. 154(b) by 677 days.

(21) Appl. No.: 17/922,524

(22) PCT Filed: May 11, 2021

(86) PCT No.: PCT/EP2021/062554

§ 371 (c)(1),
(2) Date: Oct. 31, 2022

(87) PCT Pub. No.: WO2021/239463

PCT Pub. Date: Dec. 2, 2021

(65) Prior Publication Data

US 2023/0167209 A1 Jun. 1, 2023

(30) Foreign Application Priority Data

May 29, 2020 (EP) .................................... 20177586

(51) Int. Cl.

| | |
|---|---|
| ***C08F 2/46*** | (2006.01) |
| ***A61K 6/887*** | (2020.01) |
| ***A61L 27/18*** | (2006.01) |
| ***C08F 2/48*** | (2006.01) |
| ***C08F 2/50*** | (2006.01) |
| ***C08F 122/10*** | (2006.01) |
| ***C08F 122/38*** | (2006.01) |
| ***C08G 61/04*** | (2006.01) |

(52) U.S. Cl.

CPC ........ *C08F 122/1006* (2020.02); *A61K 6/887* (2020.01); *A61L 27/18* (2013.01); *C08F 2/48* (2013.01); *C08F 122/385* (2013.01); *A61L 2400/06* (2013.01); *A61L 2430/12* (2013.01)

(58) Field of Classification Search

CPC ........ A61L 27/18; A61L 27/52; A61L 27/446; A61L 27/505; A61L 2430/12; A61L 2400/1063; A61K 6/887; A61K 31/77; C08F 122/385; C08F 122/1006; C08F 2/48; C08F 220/305; C08F 222/1063

USPC ............... 522/186, 184, 1, 6, 71, 189; 520/1

See application file for complete search history.

(56) References Cited

U.S. PATENT DOCUMENTS 7,687,657 B2 3/2010 Murer et al.
9,120,900 B2 9/2015 Grutzmacher et al.
9,701,700 B2 7/2017 Gruetzmacher et al.
10,040,810 B2 8/2018 Müller et al.
2006/0134169 A1 * 6/2006 Linhardt ................ G02B 1/043 623/6.23

FOREIGN PATENT DOCUMENTS

| | | | | |
|---|---|---|---|---|
| EP | 2444054 A1 | | 4/2012 | |
| JP | S60190424 A | | 9/1985 | |
| JP | 2007206217 A | * | 8/2007 | |
| JP | 2013205569 A | * | 10/2013 | B41C 1/1008 |
| WO | WO2006056541 | | 6/2006 | |
| WO | WO2011003772 | | 1/2011 | |
| WO | WO2014053455 | | 4/2014 | |
| WO | WO2014095724 | | 6/2014 | |
| WO | WO2019175112 | | 9/2019 | |
| WO | WO2019175319 | | 9/2019 | |

OTHER PUBLICATIONS

Nakayama, JP 2013205569 Machine Translation, Oct. 7, 2013 (Year: 2013).*

Shibuyaa, JP 2007206217 Machine Translation, Aug. 16, 2007 (Year: 2007).*

Hermes et al., "Preparation and characterization of amphiphilic membranes with lyotropic mesophases for smulation of skin permeation resistance," Pharmazie Govi Pharmazeutischer Verlag GmbH, pp. 481-486 (Jul. 1, 1995) with English translation.

Benedikt et al., "Highly Efficient Water-Soluble Visible Light Photoinitiators," J. of Polymer Sci part A, Polymer Chem., vol. 54, pp. 473-479 (Oct. 5, 2015.

Fairbanks et al., Photoinitiated polymerization of PEG-diacrylate with lithium phenyl-2,4,6-trimethylbenzoylphosphinate: polymerization rate and cytocompatibility, Biomaterials, vol. 30, pp. 6702-6707 (2009).

Huber et al., "Phosphorus-Functionalized Bis(acyl)phosphane Oxides for Surface Modification," Photoinitiator Synthesis, vol. 51, pp. 4648-4652 (2012).

Li et al., "Host/guest complex of Me-ß-CD/2,2-dimethyl-2-phenyl acetophenone for initiation of aqueous photopolymerizatoin: Kinetics and mechanism," Polymer, vol. 46, pp. 11934-11939 (2005).

Majima et al., "Phenyl-2,4,6-trimethylbenzoylphosphinates as water-soluble photoinitiators. Generation and reactivity of O-P($C_6H_5$)($O^{-}$) radical anions," Makromol. Chem., Vo. 192, pp. 2307-2315 (1991).

Müller et al., Simple One-Pot Syntheses of Water-Soluble Bis(acyl)phosphane Oxide Photoinitiators and Their Application in Surfactant-Free Emulsion Polymerization, Makromol. Rap;id Comm., vol. 36, pp. 553-557 (2015).

(Continued)

*Primary Examiner* — Jessica Whiteley

(74) *Attorney, Agent, or Firm* — Muncy, Geissler, Olds & Lowe, P.C.

(57) ABSTRACT

The invention relates to water soluble crosslinkable prepolymers for the preparation of chemically stable crosslinked polymer gels, a process for preparing the same, compositions containing the same and their use such as a medical or dental filler composition.

17 Claims, 2 Drawing Sheets

(56) References Cited

OTHER PUBLICATIONS

Tasdelen et al., "Phenacylpyridium Oxalate as a Novel Water-Soluble Photoinitiator for Free Radical Polymerization," Polymer Bulletin, vol. 59, pp. 759-766 (2008).
International Search Report dated Jul. 23, 2021 in corresponding application PCT/EP2021/062554.

* cited by examiner

FIG: 1
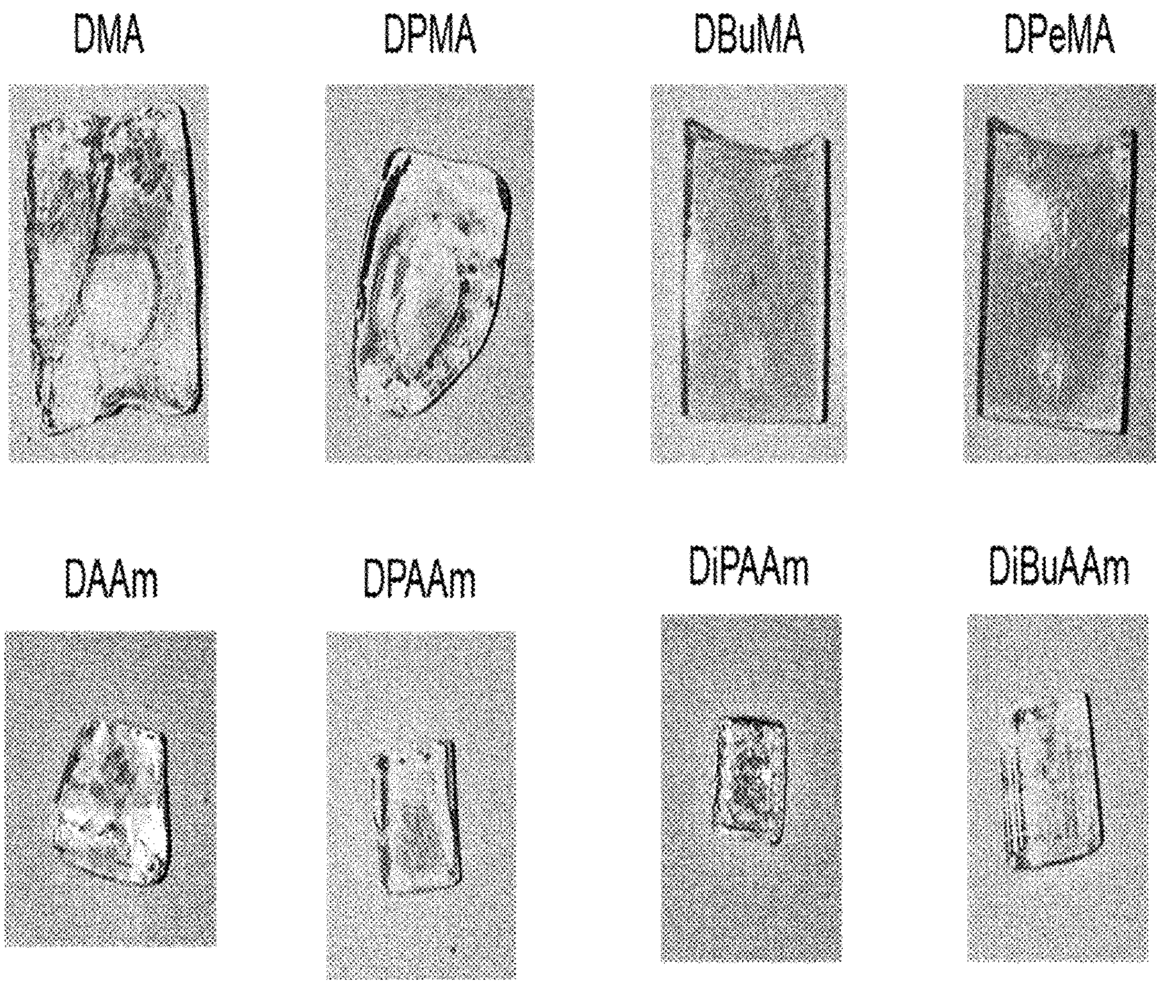

FIG: 2
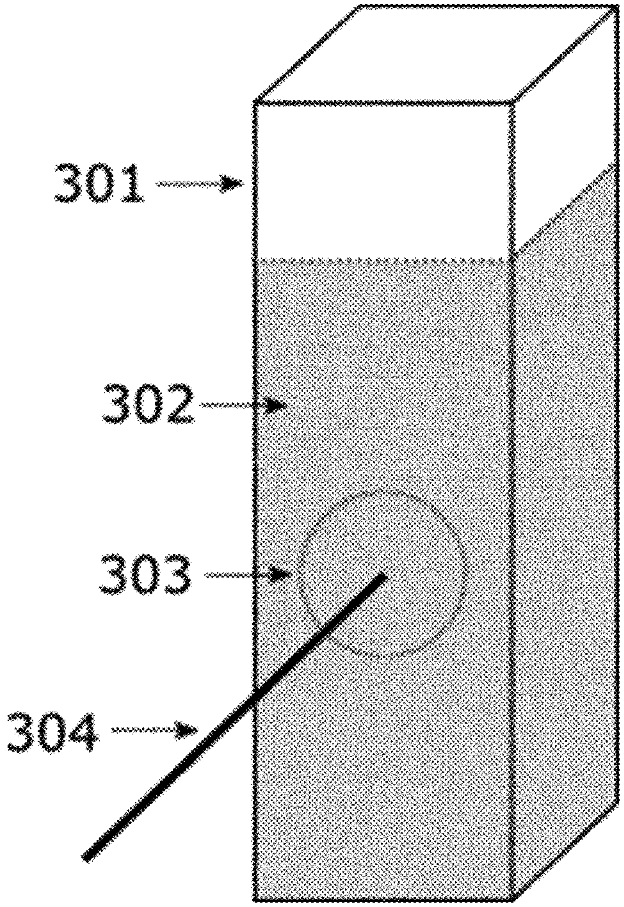

CROSSLINKABLE PREPOLYMERS FOR CHEMICALLY STABLE POLYMER GELS

CROSS REFERENCE TO RELATED APPLICATIONS

This application is a National Stage of International Application No. PCT/EP2021/062554, filed on May 11, 2021, for which priority is claimed under 35 U.S.C. § 371; and this application claims priority of Application No. 20177586.3 filed in Europe on May 29, 2020 under 35 U.S.C. § 119, the entire contents of both of which are hereby incorporated by reference.

FIELD OF THE INVENTION

The invention relates to water soluble crosslinkable prepolymers for the preparation of chemically stable crosslinked polymer gels, a process for preparing the same, compositions containing the same and their use such as a medical or dental filler composition.

BACKGROUND OF THE INVENTION

Hydrogels have been investigated for many biomedical applications (tissue engineering, wound closure, tissue adhesives & sealants). They can be obtained by chemical crosslinking of a solution of water soluble prepolymers bearing crosslinkable groups. The prepolymers can be difunctional crosslinkable derivatives of Poly(ethylene glycol) (PEG), such as PEG-dimethacrylate (PEG-DMA, CAS: 25852-47-5).

A major advantage of hydrogels is that they are water-based, and thus, their precursors are water soluble. This enables their use for a set of biomedical application requiring water as a solvent, that otherwise would not be possible. However, the inherently required hydrophilicity of the said precursors leads to a hydrophilic material, thus stronger interaction with water after crosslinking and therefore potentially higher degradation or instability with water.

In most applications of hydrogels, degradation of the materials is desired to take place under physiological conditions within days to weeks. To achieve this, stable polyethers (e.g. PEG) are often combined with hydrolytically labile polyesters (polylactic acid, polycaprolactone) in copolymers. The hydrolytic degradation of the polyester moieties renders the gel degradable.[4] However, even pure polyether-based hydrogels (e.g. made from PEG-DMA) degrade over the timeframe of weeks to months, due to the hydrolytic instability of the ester bond between the PEG-backbones and the crosslinkable endgroups. PEG-diacrylamide (PEG-DAAm, CAS: 160556-48-9) was suggested as a more hydrolytically stable alternative, which has an amide instead of an ester linkage.[1,2] However, Applicants found that hydrogels based on either PEG-DMA or PEG-DAAm degrade significantly within a couple of months under physiological conditions. The ester and amide bonds in PEG-methacrylates and PEG-acrylamides degrade unexpectedly fast even at neutral pH. Furthermore, PEG-derivatives with "inverse methacrylate" endgroups were proposed as hydrolytically stable replacements for PEG-DMA.[11-14] These derivatives show similar reaction rates in Michael-type reaction with thiols as PEG-acrylate[11] and could also be crosslinked in a free-radical process using a redox initiator system.[13] However, Applicants have found that rapid photopolymerization within 1-2 min irradiation time is not possible with such prepolymers. Therefore, crosslinkable pre-polymers with increased hydrolytic stability are essential for applications that require a long-term stability of several years.

In addition, poly(ethylene glycol) itself is known to degrade under oxidative conditions, for example when used as a coating for archeological artefacts, presumably by oxidation of the terminal OH-groups and/or the internal ether moieties.[3,8-10] The degradation of PEG-based hydrogels is thus expected to be a combination of the hydrolysis of the ester/amide bonds between the backbone and the endgroup, as well as the oxidative degradation of the ether groups in the backbone.[1,5-7] Such hydrogels were shown to degrade through internal C—O-bond oxidation when stored under air, whereas when stored in water, this effect was lowered due to the lower concentration of oxygen.[6] In addition, Applicants were able to detect oxidative degeneration products in accelerated aging experiments with PEG-DMA and PEG-DAAm based hydrogels.

Therefore, for the preparation of long-term chemically stable hydro- or polymer gels, in addition to hydrolytically stable pre-polymers, a suitable antioxidant is required. Phenols are commonly used as antioxidants to suppress oxidative degeneration in polymers, cosmetics, pharmaceuticals and food. In addition, they are commonly applied to improve the storability and shelf-life of curable monomer and polymer compositions by suppressing the free-radical polymerization. At the time of intended curing, the polymerization is inhibited or retarded, as the radicals generated from the initiator system are trapped by the stabilizers, until those are consumed. This will result in the cured formulation not containing any antioxidant, thus not being protected against oxidative degeneration which also acts through a radical process.

Therefore, an antioxidant for the preparation of prepolymer formulations, which can be converted into chemically stable crosslinked polymer gels, must sufficiently suppress oxidative degeneration, while remaining inert to the free radicals generated during the curing step in order not to inhibit this and not be consumed during this reaction. In summary, it must fulfill the following properties: Compatible with the aqueous prepolymer formulation; Not inhibiting any free radical-based polymerization/crosslinking process or being consumed during such a process, while effectively inhibiting oxygen-radical based degeneration; Retention in the crosslinked polymer gel compositions post-curing to guarantee long-term oxidative stability.

Most common, phenol-based antioxidants were found to be either not soluble in the prepolymer formulation, not stable over the required product shelf-life, or having a negative impact on the free radical polymerization.

Building on this knowledge, the purpose of the present invention is to provide water soluble crosslinkable prepolymers for the preparation of chemically stable crosslinked polymer gels, as well as compositions comprising suitable antioxidants for the preparation of chemically stable crosslinked polymer gel; which are in particular oxidatively and hydrolytically resistant and more generally, resistant to chemical degradation so as to achieve an unexpected stability in the long term.

BRIEF DESCRIPTION OF THE INVENTION

Hydrogels based on functionalized PEG-derivatives bearing hydrophobic linkers displayed remarkable stability against hydrolytic degradation as shown by the constant dry weight after accelerated aging experiments as compared to the reduced dry weight obtained with hydrogels based on PEG-DMA or PEG-DAAm. However, the aging solvent of these samples still showed traces of oxidative degradation products. When the prepolymer solution contained suitable antioxidants, these degradation products were not observed.

One of the objects of the present invention is to provide a water soluble crosslinkable prepolymer for the preparation of chemically stable crosslinked polymer gels, said water soluble crosslinkable prepolymer having the formula I:

$R^1$-L-B-L-$R^2$ (J)

where:

B is a backbone selected from the group consisting of:

Poly(ethylene glycol) (PEG):

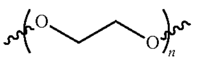

with n comprising between 1 to 450 repeating units,

Oligo(ethylene glycol) (EG):

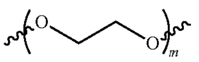

with m comprising between 1 to 12 repeating units, Poloxamer:

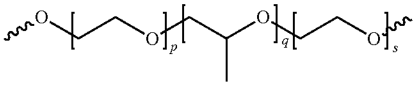

where p, q, s are independent from each other and comprise between 1 to 200 repeating units, Inverse Poloxamer:

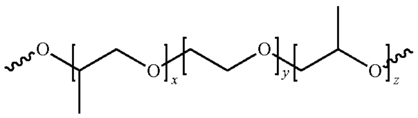

where x, y, z are independent from each other and comprise between 1 to 200 repeating units;

L is a linker selected among $C_3$ to $C_{18}$ linear or branched alkyl chains;

R1 and R2 are endgroups with R1 being equal or different from R2, where R1 and R2 are selected from the group consisting of: H, OH; acrylate; methacrylate; acrylamide; methacrylamide; but-3-en-2-one; inverse methacrylate of formula

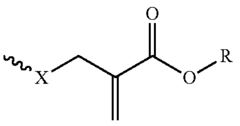

where R is an alkyl, X═O, NH; vinylsulfone; vinylurea; vinylcarbonate; vinylcarbamate; vinylthioester; vinylthiourea; with the proviso that R2 is not H or OH when R1 is H or OH;

and with the proviso that when L=$C_3$ (n-propyl, i-propyl) then endgroups R1 and R2 are not acrylamide.

Preferably, the water soluble crosslinkable prepolymer has the formula I with the proviso that when m=8, L is not C11 (undecyl).

In one embodiment, the water soluble crosslinkable prepolymer is a water soluble crosslinkable dental prepolymer for the preparation of chemically stable crosslinked dental polymer gels, said water soluble crosslinkable dental prepolymer having the formula I.

Preferably, R1 and R2 are endgroups with R1 being equal or different from R2, where R1 and R2 are selected from the group consisting of: H, OH; acrylate; methacrylate; but-3-en-2-one; inverse methacrylate of formula

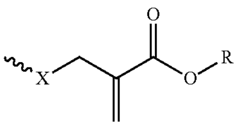

where R is an alkyl, X═O, NH; vinylsulfone; vinylurea; vinylcarbonate; vinylcarbamate; vinylthioester; vinylthiourea; with the proviso that R2 is not H or OH when R1 is H or OH.

Another object of the present invention is to provide a water soluble crosslinkable prepolymer for the preparation of chemically stable crosslinked polymer gels, said water soluble crosslinkable prepolymer having the formula II:

R1-B-R2 (II)

where:

B is a backbone consisting of:

Inverse Poloxamer:

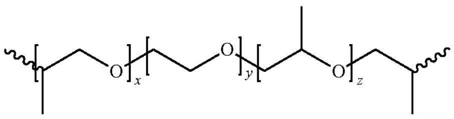

where x, y, z are independent from each other and comprise between 1 to 200 repeating units;

R1 and R2 are endgroups with R1 being equal or different from R2, where R1 and R2 are selected from the group consisting of: H, OH; acrylate; methacrylate; acrylamide; methacrylamide; but-3-en-2-one; inverse methacrylate of formula

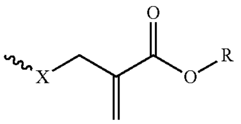

where R is an alkyl, X═O, NH; vinylsulfone; vinylurea; vinylcarbonate; vinylcarbamate; vinylthioester; vinylthiourea; with the proviso that R2 is not H or OH when R1 is H or OH.

In one embodiment, the water soluble crosslinkable prepolymer is a water soluble crosslinkable dental prepolymer for the preparation of chemically stable crosslinked dental polymer gels, said water soluble crosslinkable dental prepolymer having the formula II.

Preferably, R1 and R2 are selected from the group consisting of: H, OH; acrylate; methacrylate; but-3-en-2-one; inverse methacrylate of formula

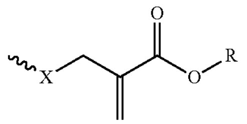

where R is an alkyl, X=O, NH; vinylsulfone; vinylurea; vinylcarbonate; vinylcarbamate; vinylthioester; vinylthiourea; with the proviso that R2 is not H or OH when R1 is H or OH.

A further object of the invention is to provide a process for preparing a chemically stable crosslinked polymer gel composition, preferably a chemically stable crosslinked dental gel composition, said process comprising the steps of:

a) dissolving the water soluble crosslinkable prepolymer as described herein in a suitable solvent;
b) adding phenolic or aminoxyl radical stabilizers;
c) adding a radical polymerization initiator;
d) applying a polymerization or crosslinking step to form said chemically stable resistant polymer gel composition.

Preferably the radical polymerization initiator is provided either as a solution in a suitable solvent or as a fine suspension.

Yet another object of the invention is to provide a precursor composition of a chemically stable crosslinked polymer gel composition, for example a dental precursor composition of a chemically stable crosslinked dental polymer gel composition. The precursor composition preferably comprises between 5-95% in weight of the stable water soluble crosslinkable prepolymer of the invention, between 5-95% in weight of a suitable solvent, between 0.001-10% in weight of phenolic or aminoxyl radical stabilizers and between 0.001-10% in weight of a radical polymerization initiator.

The invention also provides for a chemically stable crosslinked polymer gel composition obtainable by crosslinking the precursor composition according to the invention, wherein said chemically stable crosslinked polymer gel composition retains at least 95% of its initial dry mass after being stored in water at 57° C. for 8 weeks and being subsequently subjected to a washing step and a vacuum drying step to remove any water or solvents.

Also encompassed is a medical or dental filler precursor composition, preferably a dental filler precursor composition, comprising the precursor composition of the invention.

Other objects and advantages of the invention will become apparent to those skilled in the art from a review of the ensuing detailed description, which proceeds with reference to the following illustrative drawings, and the attendant claims.

BRIEF DESCRIPTION OF THE FIGURES

FIG. 1: Photographs of hydrogel samples obtained from different prepolymers during the photopolymerization efficiency tests according to application example 5.

FIG. 2: Schematic representation of the setup used to analyse the photopolymerization efficiency. The following reference numbers are given below: 301=2 mL polystyrene cuvette; 302=Liquid prepolymer composition; 303=Solidified hydrogel; 304=Laser beam.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control.

Unless defined otherwise, all technical and scientific terms used herein have the same meaning as is commonly understood by one of skill in art to which the subject matter herein belongs. As used herein, the following definitions are supplied in order to facilitate the understanding of the present invention.

As used in the specification and claims, the singular forms "a", "an" and "the" include plural references unless the context clearly dictates otherwise.

The presence of broadening words and phrases such as "one or more," "at least," "but not limited to" or other like phrases in some instances shall not be read to mean that the narrower case is intended or required in instances where such broadening phrases may be absent.

The terms "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The term "substantially" with reference to a property or characteristic means that the property or characteristic is exhibited to a greater extent than the opposite of that property or characteristic is exhibited.

Also, the use of "or" means "and/or" unless otherwise stated.

Similarly, "comprise", "comprises", "comprising", "include", "includes" and "including" are interchangeable and not intended to be limiting. The term "comprise" is generally used in the sense of include, that is to say permitting the presence of one or more features or components.

It is to be further understood that where descriptions of various embodiments use the term "comprising", those skilled in the art would understand that in some specific instances, an embodiment can be alternatively described using language "consisting essentially of" or "consisting of".

Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In the frame of the present disclosure, the term "composition" is used interchangeably with the term "formulation". A "composition", as used herein, refers to a mixture of ingredients or compounds prepared in a certain way and used for a specific purpose. The concept is also clearly linked to the process in which different compounds are combined to produce a final product.

As used herein, the term "hydrogel" refers to a gel in which the swelling agent is an aqueous solution. A hydrogel is a macromolecular polymer gel constructed of a network of crosslinked polymer chains. It is synthesized from mostly, but not only hydrophilic pre-polymers, sometimes found as a colloidal gel in which water is the dispersion medium. Hydrogels are highly absorbent natural or synthetic polymeric networks. As a result of their characteristics, hydrogels develop typical firm yet elastic mechanical properties with elastic moduli between some Pa and several M Pa, ultimate strength ranging from a few Pa to up to several tens or hundreds of MPa and deformations may range from less than 0.001% up to several thousand folds. Several physical properties of the (hydro)gels are dependent upon concentration. Increase in (hydro)gel concentration may change its pore radius, morphology, or its permeability to different molecules. One skilled in the art will appreciate that the volume or dimensions (length, width, and thickness) of a (hydro)gel can be selected based on instant needs, such as for instance the region or environment into which the (hydro)gel is to be implanted or such as whether it has to be biodegradable or not.

In polymer chemistry "cross-linking" usually refers to the use of cross-links to promote a change in the polymers' physical properties. The term cross-link is a bond that links one polymer chain to another. These links may take the form of covalent bonds (chemical cross-links) or by hydrogen bonds, hydrophobic interactions or chain entanglements (physical cross-links). The polymers can be either synthetic polymers or natural polymers. Crosslinking is the general term for the process of forming bonds or relatively short sequences of chemical bonds to join two polymer chains together. In polymer chemistry, when a synthetic polymer is said to be "cross-linked", it usually means that the entire bulk of the polymer has been exposed to the cross-linking method. The resulting modification of mechanical properties depends strongly on the cross-link density. Low cross-link densities increase the viscosities of polymer melts.

Intermediate cross-link densities transform gummy polymers into materials that have elastomeric properties and potentially high strengths. Very high cross-link densities can cause materials to become very rigid or glassy, such as phenol-formaldehyde materials. Cross-links can be formed by chemical reactions that can be initiated by heat, pressure, change in pH, or irradiation. For example, mixing of an unpolymerized or partially polymerized material with specific chemicals called crosslinking reagents results in a chemical reaction that forms cross-links. Cross-linking can also be induced in materials that are normally thermoplastic through exposure to a radiation source, such as electron beam, gamma radiation, or UV light.

The term "crosslinkable" refers to a material also herein defined as prepolymer that is capable of being "crosslinked".

The term "pre-polymer" or "prepolymer" refers to a monomer or system of monomers that has been reacted to an intermediate molecular mass state. This material is capable of further polymerization by reactive groups to a fully cured high molecular weight, cross-linked state. As such, mixtures of reactive polymers with un-reacted monomers may also be referred to as pre-polymers. The term "prepolymer" and "polymer precursor" may be interchanged. A prepolymer is a stable usually partially polymerized chemical intermediate that can be fully polymerized at a later time. The term "curing" means the hardening or partial hardening of a composition by any mechanism, e.g., by heat, light, radiation, e-beam, microwave, chemical reaction, or combinations thereof.

The term "cured" refers to a material or composition that has been hardened or partially hardened (e.g., (co)polymerized or crosslinked) by curing.

A "precursor", "precursor composition" or "polymer precursor" refers to the substance before chemical reaction (polymerization). The term "prepolymer", "polymer precursor" or "polymer intermediate" may be interchanged.

The terms "chemically stable crosslinked polymer gels" and "chemically stable crosslinked polymer gel composition" are interchangeable.

"Polymer gels" are defined widely as cross-linked polymer networks that are swollen in solvents. Crosslinked polymer gels have distinct chemical and physical properties. One of them is a drastic volume change in response to the application of an electric field and to changes in solvent composition, pH and temperature. Such properties of a polymer gel depend on the chemical structure and composition of the monomer units, the primary and higher-order structure, interactions between polymer chains and solvents, molecular motion and so on.

Especially, contrary to linear polymers, their unique properties arise from the three-dimensional network structure formed by crosslinks.

"Chemical stability" or "chemically stable" refers to the resistance of a compound to change in a chemical reaction. Some compounds are very stable and resistant to change; but others are unstable and degrade in the presence of water, solvent, air or other factors. Namely it is the tendency of a material to resist change or decomposition due to internal reaction, or due to the action of air, heat, light, pressure, etc. Chemically stable materials are less reactive and thereby more resistant to degradation. A chemical substance is said to be stable if it is not particularly reactive in the environment or during normal use and retains its useful properties on the timescale of its expected usefulness. In particular, the usefulness is retained in the presence of air, moisture or heat, and under the expected conditions of application.

In particular, chemically stable crosslinked polymer gels of the invention refer to hydrolytically and oxidatively stable or resistant gel material.

The "hydrolytic stability" is the property of a material such as the crosslinked polymer gel to resist chemical decomposition (hydrolysis) in the presence of water or moisture.

Hydrolysis is any chemical reaction in which a molecule of water breaks one or more chemical bonds. The term is used broadly for substitution, elimination, and fragmentation reactions in which water is the nucleophile. This stability for polymer gels also extends to other solvents like alcohols.

The stability or resistance to "oxidation" is the process in which a chemical substance does not change because of the addition of molecular oxygen or oxygen radicals.

Oxidation is the loss of electrons during a reaction by a molecule, atom or ion.

Oxidation occurs when the oxidation state of a molecule, atom or ion is increased. The opposite process is called reduction, which occurs when there is a gain of electrons or the oxidation state of an atom, molecule, or ion decreases.

In polymer science, the "backbone" chain of a polymer is the longest series of covalently bonded atoms that together create the continuous chain of the molecule. This science is subdivided into the study of organic polymers, which consist of a carbon backbone, and inorganic polymers which have backbones containing only main group elements.

"Linker" refers to a chemical moiety comprising a covalent bond or a chain of atoms that covalently attach at least two compounds. The linker can be linked to any synthetically feasible position of the compounds, but preferably in such a manner as to avoid blocking the compounds desired activity. Linkers are generally known in the art.

"Endgroups" are an important aspect of polymer synthesis and characterization. In polymer chemistry, endgroups are functionalities or constitutional units that are at the extremity of a macromolecule or oligomer (IUPAC). In polymer synthesis, like condensation polymerization and free-radical types of polymerization, end-groups are commonly used and can be analyzed for example by nuclear magnetic resonance (NMR) to determine the average length of the polymer. Other methods for characterization of polymers where endgroups are used are mass spectrometry and vibrational spectrometry, like infrared and Raman spectrometry. Not only are these groups important for the analysis of the polymer, but they are also useful for grafting to and from a polymer chain to create a new copolymer. Finally, they can also be used to crosslink polymers.

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or un-substituted. It will, of course, be understood that substituents are only at positions where they are chemically possible, the person skilled in the art being able to decide (either experimentally or theoretically) without inappropriate effort whether a particular substitution is possible.

Where two or more moieties are described as being "each independently" selected from a list of atoms or groups, this means that the moieties may be the same or different. The identity of each moiety is therefore independent of the identities of the one or more other moieties.

The term "alkyl" as used herein refers to saturated and unsaturated aliphatic groups, including straight-chain alkyl groups, branched-chain alkyl groups, optionally substituted with one or several radicals. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer, e.g. from 1 to 6 carbons (defined as lower alkyl). Preferably, alkyls of the invention, have one to thirty, more preferably one to twenty, even more preferably 3 to 18, more preferably 3 to eight, more preferably 3 to six, and most preferably from 4 to 6 carbon atoms and is linear or branched. The term "$C_1$-$C_6$ alkyl" represents a straight or branched alkyl chain having from 1 to six carbon atoms. Exemplary $C_1$-$C_6$ alkyl groups include methyl, ethyl, n-propyl, isopropyl, butyl, isobutyl, sec-butyl, t-butyl, pentyl, neo-pentyl, hexyl, isohexyl, and the like.

Poloxamers are nonionic triblock copolymers (PEG-PPG-PEG) composed of a central hydrophobic chain of polyoxypropylene (PPO, PPG, poly(propylene oxide), poly(propylene glycol)) flanked by two hydrophilic chains of polyoxyethylene (PEO, PEG, poly(ethylene oxide), poly (ethylene glycol)) (Almeida et al., 2013a; From: Nanostructures for Novel Therapy, 2017). Poloxamers are also known by the trade names Synperonics®, Pluronic®, and Kolliphor®.

Inverse or reverse poloxamer refers to the reverse block type of a central hydrophilic chain flanked by two hydrophobic chains (PPG-PEG-PPG), for example known under the trade name Pluronic® 10RS.

"(meth)acrylate" is a shorthand reference to acrylate, methacrylate, or combinations thereof, "(meth)acrylic" is a shorthand reference to acrylic, methacrylic, or combinations thereof; and "(meth)acryl" is a shorthand reference to acryl, methacryl, or combinations thereof.

"Inverse methacrylate" is a shorthand reference to alkyl 2-((X)methyl)acrylate, where X is the covalently bound variation as shown below:

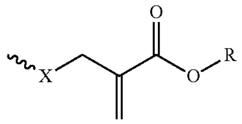

Measurement values are given including the single standard deviation for a sample set of data (68% confidence interval) behind the value with the ±sign.

One of the objects of the present invention is to provide a water soluble crosslinkable prepolymer, for example a water soluble crosslinkable dental prepolymer, for the preparation of chemically stable crosslinked polymer gels, preferably chemically stable crosslinked dental polymer gels, said water soluble crosslinkable prepolymer having the formula I:

$$R^1\text{-L-B-L-}R^2 \qquad (J)$$

where:

B is a backbone selected from the group consisting of:

Poly(ethylene glycol) (PEG):

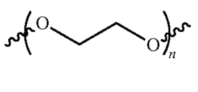

with n comprising between 1 to 450 repeating units,

Oligo(ethylene glycol) (EG):

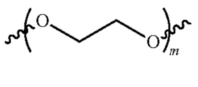

with m comprising between 1 to 12 repeating units, Poloxamer:

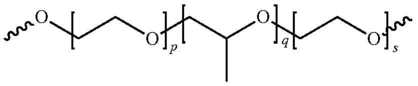

where p, q, s are independent from each other and comprise between 1 to 200 repeating units, Inverse Poloxamer:

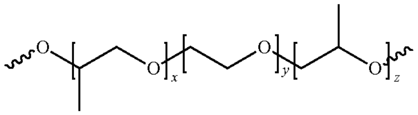

where x, y, z are independent from each other and comprise between 1 to 200 repeating units;

L is a linker selected among $C_3$ to $C_{18}$ linear or branched alkyl chains;

R1 and R2 are endgroups with R1 being equal or different from R2, where R1 and R2 are selected from the group consisting of: H, OH; acrylate; methacrylate; acrylamide; methacrylamide; but-3-en-2-one; inverse methacrylate of formula

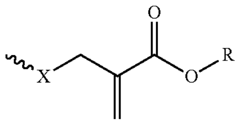

where R is an alkyl, X=O, NH; vinylsulfone; vinylurea; vinylcarbonate; vinylcarbamate; vinylthioester; vinylthiourea; with the proviso that R2 is not H or OH when R1 is H or OH;

and with the proviso that when $L=C_3$ (n-propyl, i-propyl) then endgroups R1 and R2 are not acrylamide.

Preferably, the water soluble crosslinkable prepolymer has the formula I with the proviso that when m=8, L is not C11 (undecyl)

Preferably, R1 and R2 are selected from the group consisting of: H, OH; acrylate; methacrylate; but-3-en-2-one; inverse methacrylate of formula

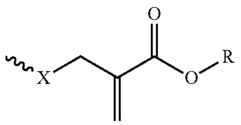

where R is an alkyl, X=O, NH; vinylsulfone; vinylurea; vinylcarbonate; vinylcarbamate; vinylthioester; vinylthiourea; with the proviso that R2 is not H or OH when R1 is H or OH;

It should be obvious to a person skilled in the art, that polymers, such as Poly(ethylene glycol) usually have no exact molecular weight but a molecular weight distribution. The molecular weight M and consequently, the number of repeating units, n, are given as average values. As opposed to this, oligomers, for example di, tri or tetra(ethylene glycol) and so on have an exact molecular weight and number of repeating units m.

Herein, the number given after the name or abbreviation of a polymer refers to its number average molecular weight ($M_n$), e.g. PEG 2k refers to Poly(ethylene glycol) with $M_n$=2000 g/mol.

Another object of the present invention is to provide a water soluble crosslinkable prepolymer, preferably a water soluble crosslinkable dental prepolymer, for the preparation of chemically stable crosslinked polymer gels, preferably chemically stable crosslinked dental polymer gels, said water soluble crosslinkable prepolymer having the formula II:

R1-B-R2 (II)

where:

B is a backbone consisting of:

Inverse Poloxamer:

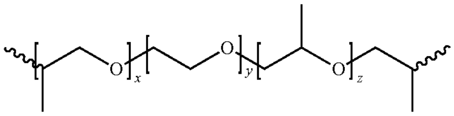

where x, y, z are independent from each other and comprise between 1 to 200 repeating units; R1 and R2 are endgroups with R1 being equal or different from R2, where R1 and R2 are selected from the group consisting of: H, OH; acrylate; methacrylate; acrylamide; methacrylamide; but-3-en-2-one; inverse methacrylate of formula

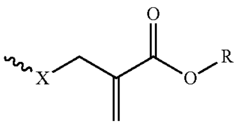

where R is an alkyl, X=O, NH; vinylsulfone; vinylurea; vinylcarbonate; vinylcarbamate; vinylthioester; vinylthiourea; with the proviso that R2 is not H or OH when R1 is H or OH.

Preferably, R1 and R2 are selected from the group consisting of: acrylate, methacrylate, acrylamide, methacrylamide, but-3-en-2-one, inverse methacrylate of formula

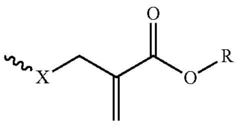

where R is an alkyl, X=O, NH; vinylsulfone.

Preferably, R1 and R2 are selected from the group consisting of: acrylate, methacrylate, but-3-en-2-one, inverse methacrylate of formula

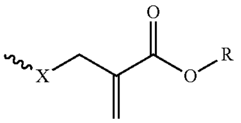

where R is an alkyl, X=O, NH; vinylsulfone.

More preferably, R1 and R2 are selected from the group consisting of: acrylate and methacrylate.

Preferably, the linker is a C4 to C6 linear or branched alkyl.

In a preferred embodiment, the water soluble crosslinkable prepolymer to be used may comprise in some embodiments one or more compounds selected from a non-exhaustive list comprising natural polymeric materials (i.e., non-synthetic polymers, polymers that can be found in nature) and/or polymers derived from the Extra Cellular Matrix (ECM) such as gelatin, elastin, collagen, agar/agarose, chitosan, fibrin, proteoglycans; a polyamino-acid or its derivatives, preferably polylysin or gelatin methyl cellulose, carbomethyl cellulose, polysaccharides and their derivatives, preferably glycosaminoglycanes such as hyaluronic acid, chondroitinsulfate, dermatansulfate, heparansulfate, heparine, keratansulfate or alginate, nucleotides, polylipides, fatty acids, poly lactic acid, lactic acid, cationic polyallylammonium chloride as well as any derivative thereof, fragment thereof and any combination thereof.

The water soluble crosslinkable prepolymer can also comprise one or several synthetic or semi-synthetic biodegradable materials. Depending on the degradation rate of the material, cells can migrate into it and possibly replace it. Examples of such materials are hydroxyapatite, poly(lactic-co-glycolic acid), lactide and glycolide polymers, caprolactone polymers, hydroxybutyric acid, polyanhydrides, polyesters, polyphosphazenes, polyphosphoesters, polycaprolactone (PCL) or a combination of PCL, caprolactone, ureido-pyrimidinone, Poly(N-isopropylacrylamide), Polyvinylpyrrolidone and poly(glycerol sebacate acrylate).

Further suitable prepolymers according to the present invention may comprise one or more compounds selected from a non-exhaustive list comprising polypropylene, polypropylenoxide or their derivatives, polymethylenoxide or its derivatives, polyethylene, polyethylenoxide or their derivatives, polyacrylate or its derivatives, poly(vinyl alcohol) (PVA) or its derivatives, poly(vinylpyrrolidone) (PVP) and its derivatives as well as combinations thereof and copolymers containing any of those polymers.

In one embodiment, the water soluble prepolymer composition comprises an antimicrobial, antibacterial, antifungal or antiviral material such as Quaternary Ammonium Compounds (QACs), cephalosporins, penicillin, aminoglycoside, gentamicin, vancomycin or undecylenic acid, an antimicrobial peptide, poly(D,1-lactide) (PDLLA), silver nano particles, or chitlac.

In most preferred embodiments, the water soluble prepolymer material is not crosslinked or minimally crosslinked in order to keep the composition in a suitable needle-injectable form. If needed, crosslinking agents and their amount can be chosen at the operator's discretion, and a person skilled in the art would easily envisage such parameters based on common practice. A further object of the invention is to provide a process for preparing a chemically stable crosslinked polymer gel composition, for example a chemically stable crosslinked dental polymer gel, said process comprising the steps of:

a) dissolving the water soluble crosslinkable prepolymer of the invention as defined above in a suitable solvent;
b) adding phenolic or aminoxyl radical stabilizers;
c) adding a radical polymerization initiator either as a solution in a suitable solvent or as a fine suspension;
d) applying a polymerization or crosslinking step to form said chemically stable resistant polymer gel composition.

It is noted that steps a)-c) are interchangeable and can be carried out in any other order provided that the last step consists in the polymerization or crosslinking according to step d).

"Phenolic radicals" or phenolic antioxidants (AOs), also known as primary antioxidants, are highly effective, non-discoloring stabilizers for organic substrates that are prone to oxidation.

They act as free radical scavengers, and are primarily used to protect the finished product namely the stable crosslinked polymer gel composition. In addition, they are commonly applied to improve the storability and shelf-life of curable monomer and polymer compositions by suppressing the free-radical polymerization.

According to a preferred embodiment, the phenolic radical stabilizers are selected from the group essentially consisting of unsubstituted or methyl, ethyl or tert-butyl substituted phenols or mixtures thereof.

"Aminoxyl radicals" are chemical species containing the R2N—O functional group. They are also known as nitroxyl radicals and nitroxides, however IUPAC discourages the use of these terms, as they erroneously suggest the presence of a nitro group. They are radicals and are structurally related to hydroxylamines and N-oxoammonium salts, with which they can interconvert via a series of redox steps. Sterically hindered aminoxyls such TEMPO and TEMPOL (4-Hydroxy-TEMPO) are persistent (stable) radicals. They are commonly used as radical scavengers, inhibitors or stabilizers. It should be obvious to a person skilled in the art, that other radical scavengers or persistent (stable) radicals such as Phenothiazine or Galvinoxyl can be used alternatively.

The term "suitable solvent" refers to a non-reactive solvent which is a solvent that does not (co)polymerize into the curable composition in which the components of the composition can be dissolved homogenously at the required concentration and do not inhibit the polymerization reaction.

According to a preferred embodiment, the suitable solvent essentially consists of water (deionized or containing ions or buffers), acetone, DMSO or alcohols or mixtures thereof. In another embodiment of the invention, the suitable solvent can contain other reagents or compounds. In yet another embodiment, these reagents or compounds are NaOCl, EDTA, HEDP, Chlorhexidine, NaOH, $Ca(OH)_2$ or other reagents that are commonly used in the cleaning, disinfection or irrigation of dental root canals.

The term "radical polymerization initiator", also referred herein as "curing agent" refers to a chemical compound which generates free radicals in order to initiate the free radical polymerization reaction. The generation of free radicals can be triggered thermally by decomposition of a thermally unstable compound ("thermal initiator") or photochemically ("photoinitiator"). It is well understood to a person skilled in the art, that the thermal activation barrier of thermal initiators can be lowered by addition of other compounds, resulting in so-called "redox" or "two-component" initiators or initiation systems.

In order to be hardened once or while injected into structures, a radical polymerization initiator, also referred herein as a "cross-linking agent" or "curing agent", is required. It is appreciated that the curing agent may be employed to chemically cross-link the water soluble crosslinkable prepolymer.

In a preferred embodiment, the curing agent is a photoinitiator. A "photoinitiator" is a molecule that creates reactive species (free radicals, cations or anions) when exposed to an electromagnetic radiation such as UV or visible light. Example of suitable visible or ultraviolet light-activated photoinitiators include ITX 4-lsopropyl-9-thioxanthenone, Lucirin TPO 2,4,6-Trimethylbenzoyl-diphenyl-phosphineoxide, Irgacure 1841-Hydroxy-cyclohexyl-phenyl-ketone, Irgacure 29591-[4-(2-Hydroxyethoxy)-phenyl]-2-hydroxy-2-methyl-1-propane-1-one, Irgacure 819 Phosphine oxide, phenyl bis(2,4,6-trimethyl benzoyl), LAP lithium phenyl-2,4,6-trimethylbenzoylphosphinate, Riboflavin 7,8-dimethyl-10-((2R,3R,4S)-2,3,4,5-tetrahydroxypentyl) benzo [g]pteridine-2,4 (31-1,1 OH)-dione, Rose Bengal 4,5,6,7-tetrachloro-2',4',5',7'-tetraiodofluorescein, PL-BDK Benzil dimethyl ketal, PL-CPK 1-hydroxy-cyclohexylphenyl-ketone, PL-HMPP 2-hydroxy-2-methyl-1-phenyl-1-propanone, Camphorquinone, 3-(4-Quantucure BPQ benzoylphenoxy)-2-hydroxy-N,N,N-trimethyl-1-propanaminium-chloride, APi-180 hydroxyalkylpropanone, bis(acyl) phosphineoxide- or mono(acyl)phosphineoxide-based initiators. In an embodiment, a bis(acyl)phosphineoxide-derived (BAPO) photoinitiator such as bis(2,4,6-trimethylbenzoyl)phosphinic acid (BAPO-OH) is used. Other examples of suitable BAPO photoinitiators are given in the following references such as: K. Dietliker, A compilation of photoinitiators commercially available for UV today, SITA Technology Ltd, Edinbergh, London, 2002; J. V. Crivello, K. Dietliker, G. Bradley, Photoinitiators for free radical cationic & anionic photopolymerisation, John Wiley & Sons, Chichester, West Sussex, England, New York, 1998.; S. Benedikt, J. Wang, M. Markovic, N. Moszner, K. Dietliker, A. Ovsianikov, H. Grutzmacher, R. Liska, J. Polym. Sci., Part A: Polym. Chem. 2016, 54, 473-479.; T. Majima, W. Schnabel, W. Weber, Makromol. Chem. 1991, 192, 2307-2315; S. Li, F. Wu, M. Li, E. Wang, Polymer 2005, 46, 11934-1 1939; M. A. Tasdelen, B. Karagoz, N. Bicak, Y. Yagci, Polymer Bulletin 2008, 59, 759-766; B. D. Fairbanks, M. P. Schwartz, C. N. Bowman, K. S. Anseth, Biomaterials 2009, 30, 6702-6707.; A. Huber, A. Kuschel, T. Ott, G. Santiso-Quinones, D. Stein, J. Brauer, R. Kissner, F. Krumeich, H. Schonberg, J. Levalois-Grutzmacher, H. Grutzmacher, Angew. Chem. 2012, 124, 4726ˆ1730.G.; Muller, M. Zalibera, G. Gescheidt, A. Rosenthal, G. Santiso-Quinones, K. Dietliker, H. Grutzmacher, Macromol. Rapid Commun. 2015, 36, 553-557, WO 2006056541, WO 2011003772, WO 2014053455, WO 2014095724, W2019175112, W2019175319.

In a particular embodiment, the radical polymerization initiator of step c) is a photoinitiator consisting of a common UV, violet, blue or other visible light active photoinitiator.

In another embodiment, the photoinitiator can be active through a multi-photon process using UV, visible or infrared light such as the two-photon absorption.

Preferably, said photoinitiator is selected from the group comprising quinones, α-hydroxy ketones, acylgermanium derivatives, bis(acyl)phosphine oxide derivatives and mono (acyl)phosphine oxide derivatives or mixtures thereof.

A further object of the invention is to provide a precursor composition of a chemically stable crosslinked polymer gel composition, wherein said precursor composition comprises between 595% in weight of the stable water soluble crosslinkable prepolymer according to the invention, between 5-95% in weight of a suitable solvent, between 0.001-10% in weight of phenolic or aminoxyl radical stabilizers and between 0.001-10% in weight of a radical polymerization initiator. Preferably, the precursor composition is a dental precursor composition of a chemically stable crosslinked dental polymer gel composition. The dental precursor composition preferably comprises between 5-95% in weight of the stable water soluble crosslinkable dental prepolymer according to the invention, between 5-95% in weight of a suitable solvent, between 0.001-10% in weight of phenolic or aminoxyl radical stabilizers and between 0.00110% in weight of a radical polymerization initiator.

A yet further object of the invention is to provide a precursor composition of a chemically stable crosslinked polymer gel composition, wherein said precursor composition comprises between 5-80% in weight of the stable water soluble crosslinkable prepolymer according to the invention, between 20-95% in weight of a suitable solvent, between 0.001-5% in weight of phenolic or aminoxyl radical stabilizers and between 0.001-5% in weight of a radical polymerization initiator.

Preferably, the precursor composition is a dental precursor composition of a chemically stable crosslinked dental polymer gel composition. The dental precursor composition preferably comprises between 5-80% in weight of the stable water soluble crosslinkable dental prepolymer according to the invention, between 20-95% in weight of a suitable solvent, between 0.001-5% in weight of phenolic or aminoxyl radical stabilizers and between 0.001-5% in weight of a radical polymerization initiator.

Those skilled in the art will appreciate that the precursor composition of the invention as described herein is susceptible to variations and modifications and that the ratios of said precursor composition can be adjusted above or below the indicated amounts.

According to an embodiment, the precursor composition further comprises between 1-90% in weight of inorganic fillers (also herein referred as additives). The inorganic filler may be included to adjust the mechanical, physical or optical properties.

Preferably, the inorganic fillers are powders or suspensions and are selected from the group comprising non-water soluble metal oxides or salts.

According to an embodiment, the precursor composition further comprises other inorganic or organic, natural or synthetic, monomeric or polymeric fillers (or additives) in order to modify and improve (mainly but not exclusively) their mechanical properties. Reinforcement using organic fibers (for example, kevlar (poly(paraphenylene terephthalamide), cellulose fibers or carbon fibers) is also possible.

The term "powder" means a dry, bulk material composed of a large number of fine particles that may flow freely when shaken or tilted.

The term "particle" or "particulate" means a substance being a solid having a shape which can be geometrically determined. The shape can be regular or irregular. Particles can typically be analysed with respect to e.g. particle size and particle size distribution. A particle can comprise one or more crystallites. Thus, a particle can comprise one or more crystal phases.

Fillers may be selected from one or more of a wide variety of materials suitable for incorporation in compositions used for example in dental applications, such as fillers currently used in dental composites and dental (e.g. crown) articles, and the like. The filler is generally non-toxic and suitable for use in the mouth. The filler can be radiopaque, radiolucent, or nonradiopaque. In some embodiments, the filler typically has a refractive index of at least 1.25, 1.3, 1.33, 1.470, 1.480, 1.500, 1.510, 1.520, 1.530, or 1.540.

Also provided is a chemically stable crosslinked polymer gel composition obtainable by crosslinking the precursor composition of the invention, wherein said chemically stable crosslinked polymer gel composition retains at least 95% of its initial dry mass after being stored in water at 57° C. for 8 weeks and being subsequently subjected to a washing step and a vacuum drying step to remove any water or solvents.

Also encompassed, is a chemically stable crosslinked polymer gel composition obtainable by the process according to the invention, wherein said chemically stable crosslinked polymer gel composition retains at least 95% of its initial dry mass after being stored in water at 57° C. for 8 weeks and being subsequently subjected to a washing step and a vacuum step to remove any water or solvents.

The invention also contemplates a medical or dental filler precursor composition, preferably a dental filler precursor composition, comprising the precursor composition according to the invention as described above.

As used herein, "medical or dental filler composition" refers to a material capable of filling out hollow structures within the human or animal body, such as but not exhaustively in veins, arteries, bone, teeth or any other natural tissue, such as to treat, heal or relieve any medical condition within the dental, neuro-, cardio-vascular or orthopedic field or any other field of human or veterinary medicine. It may further be used to adhere or bond to any natural tissue or surface. Dental filler compositions are used to fill out and seal hollow structures within teeth, jawbone or buccal mucosa. Curable dental filler compositions can further be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth that is subsequently adhered within the mouth.

Curable dental filler compositions include, for example, adhesives (e.g., dental and/or orthodontic adhesives), cements (e.g. one-part cements), primers (e.g., orthodontic primers), liners (applied to the base of a cavity to reduce tooth sensitivity), coatings such as sealants (e.g., pit and fissure sealants) and varnishes, endodontic sealants (e.g, epoxy-resin based sealants); and resin restoratives (also referred to as direct composites) such as dental fillings, as well as crowns, bridges, and articles for dental implants. Highly filled dental compositions are also used for mill blanks, from which a crown may be milled.

Surprisingly, Applicants observed that crosslinked polymer gel compositions of the invention based on the above mentioned, functionalized PEG-derivatives bearing hydrophobic linkers displayed remarkable chemical stability as shown by the constant dry weight after accelerated aging experiments as compared to the reduced dry weight obtained with crosslinked polymer gel compositions based on PEG-DMA or PEG-DAAm. The derivatives can be obtained in three to five synthetic steps from PEG, as demonstrated in examples 1-11. PEG is first converted into PEG-dimesylate, which is then reacted with an monoalkoxide of a suitable diol, followed by esterification with acryloyl or methacryloyl chloride, yielding the corresponding (meth)acrylates. To obtain the corresponding (meth)acrylamides, the linker-containing PEG is converted into the corresponding diamine via the dimesylate, followed by amidation with acryloyl or methacryloyl chloride, similar to a literature-established procedure to convert PEG into PEG DAAm.[Browning, M. B.; Cosgriff-Hernandez, E. Biomacromolecules 2012, 13 (3), 779.]

As demonstrated in comparative example 2, PEG-DMA- and also PEG-DAAm-based crosslinked polymer gel compositions degrade significantly in an aqueous environment and loose up to 18% of their dry content when aged at 57° C. for 8 weeks. Unexpectedly, crosslinked polymer gel compositions samples based on PEG-DAAm degrade to a greater degree (18.0%) than those based on PEG-DMA (12.3%), despite the amide bond in PEG-DAAm, which should be inherently more hydrolytically resistant than the ester bond in PEG-DMA. PEG-DAAm photopolymerizes and cross-links much less efficiently than PEG-DMA as demonstrated by the significantly lower polymerized mass (11% as compared to 53% in case of PEG-DMA, comparative example 1). The reduced polymerization efficiency leads to a lower degree of crosslinking and thus a more fragile gel network, which negatively impacts the chemical stability of a PEG-DAAm-based crosslinked polymer gel compositions.

Due to the combination of these disadvantages, PEG-DMA and PEG-DAAm cannot be used as precursors to crosslinked polymer gel compositions for applications in which efficient polymerization and long-term chemical stability are required. As opposed to this, the above mentioned, functionalized PEG-derivatives bearing aliphatic linkers can be polymerized efficiently and allow for the preparation of hydrogels or crosslinked polymer gel compositions of the invention with remarkable chemical stability. Thus, they are suitable precursors for crosslinked polymer gel compositions which must remain stable and not degrade, for example under physiological conditions.

As demonstrated in comparative examples 1 and 2, PEG-methacrylate derivatives bearing hydrophobic linkers, polymerize more efficiently than PEG-DMA (both 79% polymerized mass vs. 53% respectively) and maintain 100% of their dry weight even after treating at increased temperatures. In a preferred embodiment, the aliphatic linkers increase the hydrophobicity of the derivatives, which positively impacts the polymerization efficiency as well as the resistance of the crosslinked polymer gel to chemical degradation and hydrophilic attack.

The stability-enhancing effect of the linkers is further demonstrated in comparative example 3, in which non-crosslinkable compounds, bearing saturated esters instead of unsaturated methacrylate endgroups, with and without aliphatic linkers were compared in terms of their hydrolysis resistance. The hydrolysis product was clearly detected after a short time in the derivative without the linker, whereas the linker-containing derivatives remained stable.

However, PEG-containing crosslinked polymer gel compositions cannot only degrade through endgroup hydrolysis but also through oxidative degeneration. To guarantee long-term stability within oxidative environments, suitable antioxidants or stabilizers, which trap degenerative oxygen species are required.

In a preferred embodiment, suitable antioxidants fulfill the following properties: Compatible with the aqueous prepolymer formulation;

Not inhibiting any free radical-based polymerization/crosslinking process or being consumed during such a process, while effectively inhibiting oxygen-radical based degeneration;

Retention in the crosslinked polymer gel compositions post-curing to guarantee long-term oxidative stability.

Most common, phenol-based antioxidants are either not soluble in the prepolymer formulation or not stable over the required product shelf-life. In addition, many such compounds inhibit the free radical polymerization. Addition of such antioxidants to a crosslinkable prepolymer formulation decreases its crosslinking efficiency. Furthermore, such antioxidants do not protect the crosslinked polymer gel compositions from oxidative degeneration, as the antioxidants would have been consumed during the free radical crosslinking process.

Another embodiment of the invention therefore discloses suitable antioxidants, which are soluble or miscible with an aqueous prepolymer formulation, inhibit the oxidative degeneration of the crosslinked polymer gel compositions and retain within the crosslinked polymer gel network. Yet another embodiment discloses antioxidants, which, unexpectedly, inhibit the oxidative degeneration while not impacting the free-radical polymerization process and not getting consumed through this reaction (comparative example 4).

Another embodiment of the invention describes a process in which the above described chemically stable prepolymers of the invention and antioxidants are combined with a suitable radical polymerization initiator and a polymerization or cross-linking step to form chemically stable crosslinked polymer gel compositions. In one embodiment of the invention, the cross-linking is done by photopolymerization.

Another aspect of the invention are the above described precursor compositions of a chemically stable crosslinked polymer gel composition. In an embodiment, the composition further comprises inorganic or other fillers to adjust mechanical, physical or optical properties of the composition or the resulting crosslinked polymer gel composition, such as the viscosity, adhesiveness, hydrophilicity or hydrophobicity, elastic modulus, maximal strain under deformation, compressive strength, equilibrium swelling ratio, amount of expansion, internal osmotic pressure, color, refractive index or radiopacity.

Such compositions can be applied as injectable, curable fillers in the medical or dental field, preferably the dental field, or any other application where a stable, water-based material is required to fill a hollow structure or cover a surface. In a preferred embodiment, the use PEG-based prepolymers as well as the use of water as an inert, non-toxic solvent allows to prepare formulations of excellent biocompatibility. In yet another embodiment such formulations show a biocompatibility at least as high as that of a formulation containing PEG-DMA instead of the prepolymers disclosed herein, evidenced for example in a cell-viability of >70% in a in-vitro cytotoxicity assay.

In another embodiment, the adjustable viscosity allows, high surface wettability and hydrophilicity of such formulations allows them to be injected through thin cannulas or catheters (internal diameter 20 μm-1 mm) and allows complete filling of thin, small, branched or complex hollow structures (diameter 5 μm-2 mm, length 1 mm-20 cm), as opposed to existing, high-viscosity, paste-like sealers, fillers or cement, which often lead to incomplete filling, for example of the complex, branched tubular dental root canal system.

In yet another embodiment, the formulation can also be used to fill out larger, bulk structures. Conversion of the formulations into crosslinked polymer gel compositions by crosslinking thus allows the minimally invasive placement of implant materials into all parts of the human or animal body. As opposed to this, existing medical fillers for dental, orthopedic, ophthalmic, neuro- or cardiovascular applications often require the use of toxic monomers or solvents, while their high viscosity impedes application through thin cannulas or catheters.

In another preferred embodiment, the polymerization shrinkage, commonly happening upon crosslinking, is compensated by the self-expansion stemming from the uptake of water or other liquids from the surrounding environment. Thus, such formulations can be used to tightly seal hollow structures within the human or animal body, while avoiding shrinkage-based leakages and other treatment failures, for example in endodontics, where shrinkage of the sealer leads to bacterial leakage into the filled root canal and thus, re-infection of the root canal system.

Another aspect of the invention describes chemically stable crosslinked polymer gel composition obtained by the processes described above or by crosslinking the above described precursor composition. While providing the common advantages of hydrogels or other crosslinked polymer gel compositions, such as tissue-like mechanical properties, high biocompatibility, high elastic modulus, maximal strain under deformation, and compressive strength; these gels are chemically stable under physiological conditions. They can thus be applied in the medical or dental field to permanently seal cavities or other hollow structures.

In addition to the above mentioned advantages of hydrogels or other polymer gel compositions, preferably the application as an endodontic sealant benefits from the adjustable mechanical properties. It allows to prepare an endodontic sealer with mechanical properties similar to those of the natural pulp tissue and also renders the sealer easily removable, which is required in case of re-treatments.

In another embodiment of the invention, the chemically stable crosslinked polymer gel of the invention provides a resistant seal against migration or leakage of microbes, such as bacteria, which would not be the case if the polymer gel degrades over time.

In yet another embodiment, the chemically stable crosslinked polymer gel of the invention is permanently resistant against mechanical stimuli such as compression, traction or swelling of the gel. Preferably, in case of deformation/strains, that are between 0.001% and 10%. In another preferred embodiment the deformation/strains are applied cyclically to the material from 2 up to $10^9$ cycles.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1

Poly(ethylene glycol) (1 equivalent) was loaded into a round-bottom flask coupled with a magnetic stirring bar. Dichloromethane (DCM, 0.17 M) and triethylamine (1.6 equiv) were added and the solution was cooled down to 0° C. Methanesulfonyl chloride (1.25 equiv) was then added slowly and the reaction was left to stir at 0° C. for 45 min and was warmed to room temperature overnight. Once complete, the reaction was quenched with water and extracted with DCM. The aqueous phase was washed with DCM. The combined organic layer was dried over magnesium sulfate. The mixture was filtered, and the filtrate was concentrated under reduced pressure to approximately 5% volume. The resulting crude oily product was added to rapidly stirring diethyl ether at room temperature, which was stirred for 30 minutes. The mixture was then cooled to 0° C. and stirred for a further 30 minutes. The precipitate was collected via vacuum filtration over a frit, washed with diethyl ether, and was dried under high vacuum to yield the Poly(ethylene glycol) dimesylate (PEG DOMs) as a white solid. 1H NMR (DMSO-d6, 300 MHz) δ (ppm): 4.34-4.27 (m, 4H, MsOCH2), 3.72-3.63 (m, 4H, CH2), 3.51 (br s, backbone), 3.17 (s, 6H, CH3).

Example 2

A round-bottom flask coupled with a magnetic stirring bar was loaded with dry THE (0.15 M in respect to PEG DOMs) and sodium hydride (2 equiv, 60% dispersion in mineral oil) under an argon atmosphere. The solution was cooled in an ice bath and the 1,3-propanediol (2.5 equiv) was slowly added. The mixture was left to stir for at 6 hours while warming up to room temperature. Then the polyethylene glycol dimesylate (1 equiv) was slowly added to the mixture. A reflux condenser was then connected, and the reaction was heated to reflux overnight. When complete conversion was reached, the reaction mixture was cooled down to room temperature. Once cooled, water and dichloromethane were added. The aqueous phase was further extracted with dichloromethane (⅔ times). The combined organic extract was dried over magnesium sulfate and was concentrated under reduced pressure to roughly 5% volume.

The remaining residue was vigorously stirred, and diethyl ether was then added until a substantial precipitate was observed. The solution was further cooled down in an ice bath to maximize the precipitate yield. The precipitate was collected via vacuum filtration over a frit, washed with diethyl ether, and was further dried under high vacuum to yield the product as a white solid. PEG DP 2k (di-n-propyl): 1H NMR (DMSO-d6, 300 MHz) δ (ppm): 4.34 (t, J=5.2 Hz, 2H, OH), 3.51 (br s, backbone), 1.63 (p, J=6.5 Hz, 4H, CH2).

Example 3

A round-bottom flask coupled with a magnetic stirring bar was loaded with dry THE (0.15 M in respect to PEG DOMs) and sodium hydride (2 equiv, 60% dispersion in mineral oil) under an argon atmosphere. The solution was cooled in an ice bath and the 1,2-propanediol (2.5 equiv) was slowly added. The mixture was left to stir for at 5 hours while warming up to room temperature. Then the polyethylene glycol dimesylate (1 equiv) was slowly added to the mixture. A reflux condenser was then connected, and the reaction was heated to reflux overnight. When complete conversion was reached, the reaction mixture was cooled down to room temperature. Once cooled, water and dichloromethane were added. The aqueous phase was further extracted with dichloromethane (⅔ times). The combined organic extract was dried over magnesium sulfate and was concentrated under reduced pressure to roughly 5% volume.

The remaining residue was vigorously stirred, and diethyl ether was then added until a substantial precipitate was observed. The solution was further cooled down in an ice bath to maximize the precipitate yield. The precipitate was collected via vacuum filtration over a frit, washed with diethyl ether, and was further dried under high vacuum to yield the product as a white solid. PEG DiP 2k (di-i-propyl, from (S)-propane-1,2-diol): 1H NMR (DMSO-d6, 300 MHz) δ (ppm): 4.51 (d, J=4.5 Hz, 2H, OH), 3.51 (br s, backbone), 3.43-3.33 (m, 2H, CH), 1.01 (d, J=6.1 Hz, 6H, CH3).

Example 4

Other linkers were introduced in a similar manner. PEG DBu 2k (di-n-butyl): 1H NMR (DMSO-d6, 300 MHz) δ (ppm): 4.34 (t, J=5.0 Hz, 2H, OH), 3.51 (br s, backbone) 3.37 (t, J=6.0 Hz, 4H, CH2), 1.58-1.34 (m, 8H, CH2).PEG DiBu 2k (di-i-butyl): 1H NMR (DMSO-d6, 300 MHz) δ (ppm): 4.36 (t, J=5.3 Hz, 2H, OH), 3.51 (br s, backbone), 3.30-3.12 (m, 4H, CH2), 1.74 (h, J=6.6 Hz, 2H, CH), 0.83 (d, J=6.8 Hz, 6H, CH3). PEG DPe 2k (di-n-pentyl): 1H NMR (DMSO-d6, 300 MHz) δ (ppm): 4.32 (t, J=5.0 Hz, 2H, OH), 3.51 (br s, backbone), 3.36 (t, J=6.1 Hz, 4H), 1.56-1.22 (m, 12H, CH2). PEG DHe 2k (di-n-hexyl): 1H NMR (DMSO-d6, 300 MHz) δ (ppm): 4.30 (t, J=5.0 Hz, 2H, OH), 3.51 (br s, backbone), 3.36 (t, J=6.0 Hz, 4H, CH2), 1.53-1.21 (m, 16H, CH2).

Example 5

Poly(ethylene glycol) di(propan-3-ol) (PEG DP 2k, 1 equiv) was loaded in a round-bottom flask coupled with a magnetic stirring bar and dissolved in dry DCM (0.17 M). Triethylamine (1.5 equiv) was added to the solution. Methacryloyl chloride (freshly distilled, 1.3 equiv) was then added at 0° C. and the reaction was left to stir at 25° C. overnight in the dark. Once complete the mixture was passed through a column of basic alumina using DCM as eluent. The filtrate was concentrated under reduced pressure to approximately 5% volume. The resulting crude oily product was added to rapidly stirring diethyl ether at room temperature, which was stirred for 30 minutes. The mixture was then cooled to 0° C. and stirred for a further 30 minutes. The precipitate was collected via vacuum filtration over a frit, washed with diethyl ether, and was dried under high vacuum to yield the product as a white solid. PEG DPMA 2k (di-n-propyl methacrylate): 1H NMR (CDCl3, 300 MHz) δ (ppm): 6.01 (dd, J=0.8, 1.7 Hz, 2H, vinyl), 5.47 (t, J=1.7 Hz, 2H, vinyl), 4.16 (t, J=6.4 Hz, 4H, CO2CH2), 3.57 (br s, backbone), 3.49 (t, J=6.4 Hz, 4H, CH2), 1.92-1.84 (m, 4H, CH2), 1.86 (s, 6H, CH3); 13C NMR (CDCl3, 300 MHz) δ (ppm): 167.3, 136.3, 125.2, 70.6, 70.5, 70.2, 67.7, 61.8, 28.9, 18.2.

Example 6

Poly(ethylene glycol) di(propan-2-ol) (PEG DiP 2k, 1 equiv) was loaded in a round-bottom flask coupled with a magnetic stirring bar and dissolved in dry DCM (0.17 M). Triethylamine (1.5 equiv) was added to the solution. Methacryloyl chloride (freshly distilled, 1.3 equiv) was then added at 0° C. and the reaction was left to stir at 25° C. overnight in the dark. Once complete the mixture was passed through a column of basic alumina using DCM as eluent. The filtrate was concentrated under reduced pressure to approximately 5% volume. The resulting crude oily product was added to rapidly stirring diethyl ether at room temperature, which was stirred for 30 minutes. The mixture was then cooled to 0° C. and stirred for a further 30 minutes. The precipitate was collected via vacuum filtration over a frit, washed with diethyl ether, and was dried under high vacuum to yield the product as a white solid. PEG DiPMA 2k (di-i-propyl methacrylate): 1H NMR (CDCl3, 300 MHz) δ (ppm): 6.08 (s, 1H), 5.52 (s, 1H), 5.17-5.01 (m, 1H), 4.31-4.22 (m, 1H), 4.13-4.04 (m, 1H), 3.62 (s, backbone), 1.91 (s, 3H), 1.23 (d, J=6.4 Hz, 3H); 13C NMR (CDCl3, 300 MHz) δ (ppm): 136.60, 125.38, 73.70, 70.55, 69.78, 18.35, 16.70.

Example 7

Other esterification reactions were carried out in a similar manner.

PEG DMA 2k (dimethacrylate): 1H NMR (CDCl3, 300 MHz) δ (ppm): 6.10 (s, 2H, vinyl), 5.54 (s, 2H, vinyl), 4.35-4.17 (m, 4H, CO2CH2), 3.77-3.66 (m, 4H), 3.61 (br s, backbone), 1.92 (s, 6H, CH3); 13C NMR (CDCl3, 300 MHz) δ (ppm): 166.9, 135.8, 125.4, 70.3, 68.8, 63.6, 18.1. PEG DBuMA 2k (di-n-butyl methacrylate): 1H NMR (CDCl3, 200 MHz) δ (ppm): 6.07 (s, 2H, vinyl), 5.52 (s, 2H, vinyl), 4.14 (t, J=6.1 Hz, 4H, CO2CH2), 3.62 (br s, backbone), 3.47 (t, J=6.1 Hz, 4H, CH2), 1.91 (s, 6H, CH3), 1.81-1.55 (m, 8H); 13C NMR (CDCl3, 300 MHz) δ (ppm): 167.5, 136.5, 125.4, 70.9, 70.7, 70.7, 70.3, 64.6, 26.3, 25.5, 18.4. PEG DiBuMA 2k (di-i-butyl methacrylate): 1H NMR (CDCl3, 300 MHz) δ (ppm): 6.04 (s, 2H, vinyl), 5.50 (s, 2H, vinyl), 4.09 (dd, J=10.8, 5.7 Hz, 2H, CH2), 4.00 (dd, J=10.9, 6.1 Hz, 2H, CH2), 3.59 (s, backbone), 3.42-3.29 (m, 6H, CH3), 2.11 (h, J=6.4 Hz, 2H, CH), 1.89 (s, 6H, CH3), 0.93 (d, J=6.9 Hz, 6H, CH3); 13C NMR (CDCl3, 300 MHz) δ (ppm): 167.4, 136.5, 125.3, 73.3, 70.6, 66.7, 33.3, 18.4, 14.1. PEG DPeMA 2k (di-n-pentyl methacrylate): 1H NMR (CDCl3, 200 MHz) δ (ppm): 6.09 (s, 2H, vinyl), 5.54 (s, 2H, vinyl), 4.14 (t, J=6.5 Hz, 4H, CO2CH2), 3.64 (br s, backbone), 3.47 (t, J=6.3 Hz, 4H, CH2), 1.94 (s, 6H, CH3), 1.80-1.54 (m, 8H), 1.52-1.36 (m, 4H); 13C NMR (CDCl3, 300 MHz) δ (ppm): 167.6, 136.6, 125.30, 71.2, 70.7, 70.2, 64.7, 29.3, 28.5, 22.7, 18.4. PEG DHeMA 2k (di-n-hexyl methacrylate): 1H NMR (CDCl3, 200 MHz) δ (ppm): 6.05 (s, 2H, vinyl), 5.51 (s, 2H, vinyl), 4.10 (t, J=6.5 Hz, 4H, CO2CH2), 3.63-3.36 (br s, backbone), 1.90 (s, 6H, CH3), 1.76-1.45 (m, 8H), 1.44-1.27 (m, 8H); 13C NMR (CDCl3, 300 MHz) δ (ppm): 167.5, 136.5, 125.2, 71.3, 70.6, 70.1, 64.7, 29.6, 28.6, 25.9, 25.8, 18.4.

Example 8

Poly(ethylene glycol) dimesylate was transferred into a round-bottom flask coupled with a magnetic stirring bar. 25% aqueous ammonia solution (approx. 5 mL/mmol or until the viscosity is reduced) was added into the flask, which was tightly sealed with a stopper and metal clamp.

The reaction was vigorously stirred for approx. 3 days. Once full conversion was confirmed by H NMR, the aqueous layer was extracted ¾ times with dichloromethane and the combined organic extracts were dried over magnesium sulfate and concentrated under reduced pressure but only to a viscous oil. The remaining residue was vigorously stirred, and diethyl ether was then added until a substantial precipitate was observed. The solution was further cooled down in an ice bath to maximize the precipitate yield. The precipitate was collected via vacuum filtration over a frit, washed with diethyl ether, and was further dried under high vacuum to yield the product as a white solid. PEG DAm 2k (diamine): 1H NMR (DMSO-d6, 300 MHz) δ (ppm): 3.51 (br s, backbone), 3.36 (t, J=5.8 Hz, 4H, CH2), 2.66 (t, J=5.7 Hz, 4H, CH2).

Example 9

Other aminations reactions were carried out in a similar manner from their respective dimesylated compounds. PEG DPAm 2k (di-n-propyl amine): 1H NMR (DMSO-d6, 300 MHz) δ (ppm): 4.24 (t, J=6.3 Hz, 4H, NH2), 3.51 (br s, backbone), 3.15 (s, 4H, CH2), 1.89 (p, J=6.2 Hz, 4H, CH2). PEG DiPAm 2k (di-i-propyl amine): 1H NMR (DMSO-d6, 300 MHz) δ (ppm): 4.51 (d, J=4.6 Hz, 4H, NH2), 3.51 (br s, backbone), 1.01 (d, J=6.2 Hz, 6H, CH3). PEG DBuAm 2k (di-n-butyl amine): 1H NMR (CDCl3, 300 MHz) δ (ppm): 3.54 (br s, backbone), 3.37 (t, J=6.2 Hz, 4H, OCH2), 2.61 (t, J=6.8 Hz, 4H, OCH2), 1.58-1.29 (m, 8H, CH2). PEG DiBuAm 2k (di-i-butyl amine): 1H NMR (DMSO-d6, 300 MHz) δ (ppm): 3.51 (br s, backbone), 1.63 (o, J=6.7 Hz, 2H, CH), 0.82 (d, J=6.7 Hz, 6H, CH3). PEG DPeAm 2k (di-n-pentyl amine): 1H NMR (CDCl3, 300 MHz) δ (ppm): 3.64 (br s, backbone), 3.50 (t, J=5.8 Hz, 4H, OCH2), 2.96 (t, J=7.0 Hz, 4H, OCH2), 1.82-1.41 (m, 12H, CH2). PEG DHeAm 2k (di-n-hexyl amine): 1H NMR (CDCl3, 300 MHz) δ (ppm): 3.64 (br s, backbone), 3.46 (t, J=6.7 Hz, 4H, OCH2), 2.80 (t, J=7.2 Hz, 4H, OCH2), 1.67-1.46 (m, 8H, CH2), 1.43-1.28 (m, 8H, CH2).

Example 10

Poly(ethylene glycol) diamine (1 equiv) was loaded into a round-bottom flask coupled with a magnetic stirring bar and dissolved in dichloromethane (0.18 M). Acryloyl chloride (distilled, 1.65 equiv) was added followed by sodium hydroxide solution (1 M, 1.6 equiv). The biphasic solution was vigorously stirred at 25° C. for 1.5 h (can be up to 5 h). After the reaction reached completion (evaluated by H NMR), sodium hydroxide solution (1 M, 1.6 equiv) was added and the mixture was stirred for 5 min. The mixture was transferred into a separatory funnel and the aqueous layer was extracted with DCM. The organic phase was passed through a plug of basic alumina (solution discolours). The plug was washed with DCM as eluent. The solvent was then removed under reduced pressure but only to a viscous oil. The remaining residue was vigorously stirred. Diethyl ether was then added until more noticeable precipitation was observed. The solution was further cooled down in an ice bath to maximize the precipitate yield. The precipitate was collected via vacuum filtration over a frit, washed with diethyl ether. The white powder was dried under high vacuum to remove the ether and was then lyophilized to remove water. PEG DAAm 2k (diacrylamide): 1H NMR (CDCl3, 300 MHz) δ (ppm): 6.54 (br s, 2H, NH), 6.28 (dd, J=1.5, 17.0 Hz, 2H, vinyl), 6.14 (dd, J=10.0, 17.0 Hz, 2H, vinyl), 5.61 (d, J=10.0 Hz, 2H, vinyl), 3.63 (br s, backbone), 3.52 (dd, J=5.0, 10.1 Hz, 4H, CH2); 13C NMR (CDCl3, 300 MHz) δ (ppm): 165.7, 131.2, 126.2, 70.7, 70.4, 69.9, 39.4.

Example 11

Other amidations reactions were carried out in a similar manner from their respective diamino compounds. PEG DPAAm 2k (di-n-propyl acrylamide): 1H NMR (CDCl3, 300 MHz) δ (ppm): 6.66 (br s, 2H, NH), 6.25 (d, J=16.9 Hz, 2H, vinyl), 6.11 (dd, J=17.0, 10.1 Hz, 2H, vinyl), 5.58 (d, J=10.0 Hz, 2H, vinyl), 3.63 (br s, backbone), 1.86-1.76 (m, 4H, CH2); 13C NMR (CDCl3, 300 MHz) δ (ppm): 165.8, 131.3, 126.0, 70.7, 70.3, 70.1, 38.4, 28.7. PEG DiPAAm 2k (di-i-propyl acrylamide): 1H NMR (D20, 300 MHz) δ (ppm): 6.31 (dd, J=17.1, 9.7 Hz, 2H, vinyl), 6.21 (dd, J=17.1, 1.9 Hz, 2H, vinyl), 5.79 (dd, J=9.6, 1.9 Hz, 2H, vinyl), 3.74 (br s, backbone), 3.32 (t, J=5.9 Hz, 4H, NCH2), 1.68-1.54 (m, 6H, CH3); 13C NMR (D20, 300 MHz) δ (ppm): 168.3, 130.2, 127.1, 70.5, 69.6, 69.2, 39.1, 26.1, 25.1. PEG DiBuAAm 2k (di-i-butyl acrylamide): 1H NMR (D20, 300 MHz) δ (ppm): 6.33 (dd, J=17.1, 9.8 Hz, 2H, vinyl), 6.22 (d, J=16.3 Hz, 2H, vinyl), 5.81 (d, J=10.5 Hz, 2H, vinyl), 3.74 (br s, backbone), 3.57-3.41 (m, 4H, CH2), 3.38-3.17 (m, 4H, CH2), 2.07 (o, J=6.9 Hz, 2H, CH), 0.97 (d, J=6.8 Hz, 6H, CH3); 13C NMR (D20, 300 MHz) δ (ppm): 168.4, 130.2, 127.2, 74.2, 69.6, 42.5, 33.1, 14.3. PEG DBuAAm 2k (di-n-butyl acrylamide):1H NMR (DMSO-d6, 300 MHz) δ (ppm): 6.20 (dd, J=17.1, 9.9 Hz, 1H), 6.05 (dd, J=17.1, 2.5 Hz, 1H), 5.55 (dd, J=9.9, 2.5 Hz, 1H), 3.51 (s, 131H), 3.42-3.34 (m, 2H), 3.17-3.07 (m, 2H), 1.55-1.42 (m, 6H); 13C NMR (DMSO-d6, 300 MHz) δ (ppm): 164.37, 131.86, 124.68, 69.75, 69.46, 38.28, 26.69, 25.83. PEG DPeAAm 2k (di-n-pentyl acrylamide): 1H NMR (DMSO-d6, 300 MHz) δ 8.03 (t, J=5.6 Hz, 2H, NH2), 6.20 (dd, J=17.1, 9.9 Hz, 2H, vinyl), 6.05 (dd, J=17.1, 2.5 Hz, 2H, vinyl), 5.55 (dd, J=9.9, 2.5 Hz, 2H, vinyl), 3.51 (s, backbone), 3.37 (t, J=6.5 Hz, 6H, OCH2), 3.11 (q, J=6.5 Hz, 4H, NCH2), 1.57-1.19 (m, 17H); 1H NMR (CDCl3, 300 MHz) δ 6.25 (dd, J=17.0, 1.7 Hz, 2H, vinyl), 6.08 (dd, J=17.0, 10.1 Hz, 2H, vinyl), 5.93 (s, 2H, NH2), 5.58 (dd, J=10.1, 1.8 Hz, 2H, vinyl), 3.62 (s, backbone), 3.44 (t, J=6.2 Hz, 8H, OCH2), 3.30 (q, J=6.7 Hz, 5H, NCH2), 1.55 (dq, J=11.7, 7.2 Hz, 11H), 1.38 (tt, J=10.8, 5.9 Hz, 6H); 13C NMR (DMSO-d6, 300 MHz) δ 164.4, 131.9, 124.6, 69.8, 38.5, 29.0, 28.9, 28.9, 23.2. PEG DHeAAm 2k (di-n-hexyl acrylamide): 1H NMR (DMSO-d6, 300 MHz) δ 8.02 (t, J=5.6 Hz, 2H, NH2), 6.20 (dd, J=17.1, 9.9 Hz, 2H, vinyl), 6.05 (dd, J=17.1, 2.5 Hz, 2H, vinyl), 5.54 (dd, J=9.9, 2.5 Hz, 2H, vinyl), 3.51 (s, backbone), 3.36 (t, J=6.5 Hz, 9H, OCH2), 3.10 (q, J=6.6 Hz, 5H, NCH2), 1.58-1.13 (m, 25H); 1H NMR (CDCl3, 300 MHz) δ 6.24 (dd, J=17.0, 1.7 Hz, 2H, vinyl), 6.07 (dd, J=17.0, 10.1 Hz, 2H, vinyl), 5.86 (s, 2H, NH2), 5.57 (dd, J=10.1, 1.8 Hz, 2H, vinyl), 3.61 (s, backbone), 3.46-3.34 (m, 9H, OCH2), 3.28 (td, J=7.2, 5.9 Hz, 5H, NCH2), 1.53 (dq, J=14.1, 6.8, 5.2 Hz, 13H), 1.33 (dd, J=7.1, 3.7 Hz, 13H); 13C NMR (DMSO-d6,300 MHz) δ 164.3, 131.9, 124.6, 69.8, 29.2, 29.1, 29.0, 26.3, 25.5, 25.4.

Example 12

Pluronic® 1ORS (1 equiv) was loaded in a round-bottom flask coupled with a magnetic stirring bar and dissolved in dry DCM (0.1 M). Dry triethylamine (2 equiv) was added to the solution. Methacryloyl chloride (freshly distilled, 1.75 equiv) was then added at 0° C. and the reaction was left to stir at 25° C. overnight in the dark. After completion, the reaction was quenched with water and extracted with DCM. The combined organic extracts were passed through a plug of basic alumina, which was eluted with DCM. The solvent was then removed under reduced pressure to a viscous oil. The crude oily residue was dissolved in water and was dialyzed in Spectra/Por 6 membrane tubing against water for 24 hours. The dialyzed solution was then lyophilized to dryness to yield the product 1ORS-DMA as a viscous colourless oil. 1H NMR (CDCl3, 300 MHz) δ (ppm): 6.08 (dd, J=1.0, 1.8 Hz, 2H, vinyl), 5.53-5.52 (m, 2H, vinyl), 5.09-5.02 (m, 1H, CH), 3.63-3.36 (m, PEG and PPG CH backbone), 3.41 (t, J=6.5 Hz, 4H, CH2), 1.92 (m, 6H, CH3), 1.26-1.23 (m, 6H, CH3), 1.13-1.11 (m, PPG CH3 backbone); 13C NMR (CDCl3, 300 MHz) δ (ppm): 167.1, 136.8, 125.3, 75.6, 75.5, 75.3, 75.3, 70.7, 70.7, 18.4, 17.5, 17.4, 16.9.

Application Example 1

Hydrogel samples were prepared by pipetting a solution of prepolymer prepared according to examples 5-7, 10 or 11 (30% w/w), photoinitiator (0.25% w/w), and deionized water (69.75% w/w) into a cylindrical sample mould (V=250 μL, ø=8 mm, height=5 mm) and photopolymerizing it using a blue light source of 400-460 nm wavelength.

Application Example 2

The stability of the hydrogel samples prepared according to application example 1 was studied in accelerated aging experiment: the hydrogel samples were immersed in deionized water for 8 weeks at 57° C. to accelerate the aging process. At the end of the aging period, the hydrogels were removed, dried in a vacuum oven, and then weighed. The dry content was compared to the dry content of non-aged samples and the loss of dry content was used as a measure for material degradation.

Application Example 3

The influence of different antioxidants on hydrogel stability was studied by doping prepolymer formulations with specified antioxidants prior to photopolymerization as described in application example 1, followed by accelerated aging experiments in heavy water (D20).

Detection of decomposition was observed by NMR spectroscopy with the formation of decomposition markers, such as formic acid, in the liquid. This was quantified with the addition of an internal standard.

Application Example 4

The retainment properties of antioxidants were tested by preparing and aging antioxidant-doped samples according to application example 3. The heavy water the hydrogels samples were aged in was exchanged weekly, followed by testing of the heavy water. Detection of decomposition was observed by NMR spectroscopy with the formation of decomposition markers, such as formic acid, in the liquid. This was quantified with the addition of an internal standard.

Application Example 5

The photopolymerization efficiency was examined by gravimetric determination of the cured polymer mass: Solutions containing prepolymer prepared according to examples 5-7, 10 or 11 (15% w/w) and photoinitiator (0.1% w/w) were prepared in deionized water. 500 mg of the premixed solutions were loaded into a 2 mL polystyrene cuvette and irradiated for 60 s with a laser (X=405 nm, p=10 mW) from the side. The solid hydrogels were removed, wiped to remove residual liquid, and weighed. The ratio of solid, cure material to liquid, uncured material was calculated and used as a measure for the photopolymerization efficiency. Some results of this experiment are shown in FIG. 1. The setup used is depicted in FIG. 2: 301 represents the polystyrene cuvette, 302 the liquid prepolymer composition, 303 the solidified hydrogel and 304 the laser beam.

Comparative Example 1

The photopolymerization efficiency of the prepolymers PEG-DMA (prepared according to example 7), linker-containing PEG-dimethacrylates (example 5-7), PEG-DAAm (example 10), linker-containing PEG-diacrylamides (example 11) and 1OR5-Dimethacrylate (example 12) was compared according to application example 5:

| Prepolymer | Polymer mass | Prepolymer | Polymer mass |
|---|---|---|---|
| DMA 6k | 43% | DAAm 2k | 11% |
| DMA 2k | 53% | DPAAm 2k | 6% |
| DPMA 2k | 43% | DiPAAm 2k | 6% |
| DIPMA 2k | 66% | DiBuAAm 2k | 8% |
| DiBuMA 2k | 83% | DBuAAm 2k | 5% |
| DBuMA 2k | 79% | DPeAAm 2k | 4% |
| DPeMA 2k | 79% | DHeAAm 2k | 8% |
| DHeMA 2k | 72% | 10R5-DMA | 92% |

Comparative example 2 The stability of hydrogel samples prepared from the prepolymers PEG-DMA (prepared according to example 7), linker-containing PEG-dimethacrylates (example 5-7), PEG-DAAm (example 10), linker-containing PEG-DPAAm (example 11) and 1ORS-Dimethacrylate (example 12) was compared according to application example 2:

| Prepolymer | RDC |
|---|---|
| DMA 2k | 87.7 ± 2.7% |
| DPMA 2k | 100.2 ± 0.7% |
| DBuMA 2k | 99.0 ± 0.6% |
| DiBuMA 2k | 97.5 ± 1.0% |
| DPeMA 2k | 98.8 ± 1.9% |
| DHeMA 2k | 97.6 ± 0.6% |
| DAAm 2k | 82.0 ± 2.5% |
| DPAAm 2k | 67.1 ± 2.7% |
| 10R5-DMA | 103.3 ± 1.9% |

Comparative example 3 A model comparative hydrolysis test was carried out with PEG diisobutyrate and PEG di(butane-1,4-diyl isobutyrate) in heavy water at a concentration of 30% w/w. After accelerated aging for 10 days at 57° C. in the presence of MEHQ (0.5% w/w), the hydrolysis product (isobutyric acid) was only observed in PEG diisobutyrate by 1H NMR spectroscopy, whereas the derivative with the butyl linker (PEG di(butane-1,4-diyl isobutyrate)), did not show any hydrolysis product.

Comparative Example 4

Antioxidant testing according to application example 3 showed that with the addition of BHT (with 1% DMSO) or sodium fenozan to the prepolymer formulation no decomposition was observed, which was indicated by the absence of the decomposition marker. In contrast hydrogel samples containing no antioxidant displayed substantial amounts of the marker (1.2 mM) after one week of accelerated aging. At the same time, no reduction of polymerized masses was observed in the photopolymerization efficiency tests according to application example 5 in the presence of these antioxidants.

Comparative Example 5

Retainment of BHT and sodium fenozan was studied according to application example 5. Retainment of BHT in hydrogel samples was proven by leaching experiments over three weeks by the lack of decomposition markers and antioxidant in the leached solvent, whereas samples containing sodium fenozan displayed decomposition markers after 3 weeks (1.4 mM).

REFERENCES

[1]M. B. Browning, S. N. Cereceres, P. T. Luong, E. M. Cosgriff-Hernandez, J. Biomed. Mater. Res. Part A 2014, 102, 4244-4251.

[2]M. B. Browning, Elizabeth. Cosgriff-Hernandez, Biomacromolecules 2012, 13, 779-786.

[3]J. Glastrup, Polymer Degradation and Stability 2003, 81, 273-278.

[4]A. T. Metters, K. S. Anseth, C. N. Bowman, Polymer 2000, 41, 3993-4004.

[5]Z. Stillman, B. M. Jarai, N. Raman, P. Patel, C. A. Fromen, Polym. Chem. 2020, 11, 568-580.

[6]M. Vandenhaute, D. Snoeck, E. Vanderleyden, N. De Belie, S. Van Vlierberghe, P. Dubruel, Polymer Degradation and Stability 2017, 146, 201-211.

[7]B. Reid, M. Gibson, A. Singh, J. Taube, C. Furlong, M. Murcia, J. Elisseeff, J Tissue Eng Regen Med 2015, 9, 315-318.

[8]T. Padfield, J. Winslow, W. B. Pedersen, J. Glastrup, 1990.

[9]J. Glastrup, Polymer Degradation and Stability 1996, 52, 217-222.

[10]S. Han, C. Kim, D. Kwon, Polymer 1997, 38, 317-323.

[11]X. Tong, J. Lai, B. Guo, Yanbin. Huang, J. Polym. Sci., Part A: Polym. Chem. 2011, 49, 1513-1516.

[12]Y. Tao, X. Tong, Y. Zhang, J. Lai, Y. Huang, Y. Jiang, B.-Hua. Guo, Acta Biomaterialia 2013,9,5022-5030.

[13]J. Chang, Y. Tao, B. Wang, X. Yang, H. Xu, Y. Jiang, B. Guo, Yanbin. Huang, Polymer 2014, 55, 4627-4633.

[14]J. Chang, Y. Tao, B. Wang, B. Guo, H. Xu, Y. Jiang, Yanbin. Huang, J. Mater. Chem. B 2015, 3, 1097-1105.

The invention claimed is:

1. A process for preparing a chemically stable crosslinked dental polymer gel composition, said process comprising the steps of:

a) dissolving either:

i) a water soluble crosslinkable dental prepolymer for the preparation of chemically stable crosslinked polymer gels, said water soluble crosslinkable prepolymer having the formula I:

$$R^1\text{-L-B-L-}R^2 \quad (I)$$

where:

B is a backbone selected from the group consisting of:

Poly(ethylene glycol) (PEG):

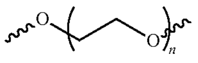

with n comprising between 1 to 450 repeating units,

Oligo(ethylene glycol) (EG):

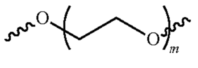

with m comprising between 1 to 12 repeating units,

Poloxamer:

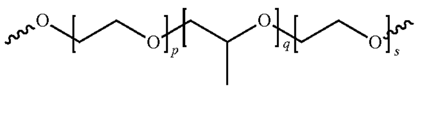

where p, q, s are independent from each other and comprise between 1 to 200 repeating units, Inverse Poloxamer:

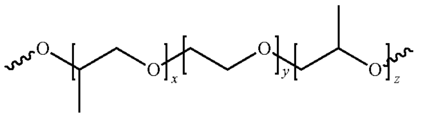

where x, y, z are independent from each other and comprise between 1 to 200 repeating units;

L is a linker selected among $C_3$ to $C_{18}$ linear or branched alkyl chains;

$R^1$ and $R^2$ are endgroups with $R^1$ being equal or different from $R^2$, where $R^1$and $R^2$ are selected from the group consisting of: H, OH; acrylate; methacrylate; acrylamide; methacrylamide; but-3-en-2-one; inverse methacrylate of formula

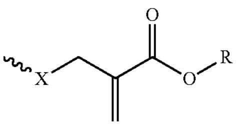

where R is an alkyl, X═O, NH; vinylsulfone; vinylurea; vinylcarbonate;

vinylcarbamate; vinylthioester; vinylthiourea; with the proviso that $R^2$is not H or OH when $R^1$is H or OH;

and with the proviso that when L=C3, then endgroups $R^1$ and $R^2$ are not acrylamide; or ii) a water soluble crosslinkable dental prepolymer for the preparation of chemically stable crosslinked polymer gels, said water soluble crosslinkable prepolymer having the formula II:

$R^1$-B-$R^2$ (II)

where:

B is a backbone consisting of:

Inverse Poloxamer:

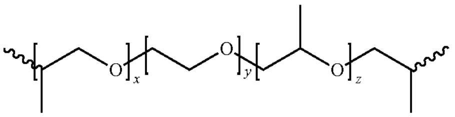

where x, y, z are independent from each other and comprise between 1 to 200 repeating units;

$R^1$ and $R^2$ are endgroups with $R^1$ being equal or different from $R^2$, where $R^1$ and $R^2$ are selected from the group consisting of: H, OH; acrylate;

methacrylate; acrylamide; methacrylamide; but-3-en-2-one; inverse methacrylate of formula

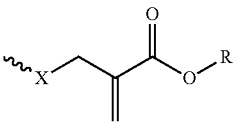

where R is an alkyl, X═O, NH; vinylsulfone; vinylurea;

vinylcarbonate; vinylcarbamate; vinylthioester; vinylthiourea; with the proviso that $R^2$ is not H or OH when $R^1$ is H or OH, in a suitable solvent;

b) adding phenolic or aminoxyl radical stabilizers;

c) adding a radical polymerization initiator;

d) applying a polymerization or crosslinking step to form said chemically stable crosslinked dental polymer gel composition.

2. The process according to claim 1, wherein the radical polymerization initiator of step c) is a photoinitiator consisting of a UV, violet, blue or other visible light active photoinitiator.

3. The process according to claim 2, wherein said photoinitiator is selected from the group comprising quinones, α-hydroxy ketones, acylgermanium derivatives, bis(acyl) phosphine oxide derivatives and mono(acyl)phosphine oxide derivatives or mixtures thereof.

4. The process according to claim 1, wherein said phenolic radical stabilizers are selected from the group essentially consisting of unsubstituted or methyl, ethyl, isopropyl or tert-butyl substituted phenols or mixtures thereof.

5. The process according to claim 1, wherein said suitable solvent essentially consists of water, acetone, DMSO or alcohols, or mixtures thereof.

6. A precursor composition of a chemically stable crosslinked dental polymer gel composition, wherein said precursor composition comprises between 5-95% in weight of either:

i) a stable water soluble dental crosslinkable prepolymer for the preparation of chemically stable crosslinked polymer gels, said water soluble crosslinkable prepolymer having the formula I:

$R^1$-L-B-L-$R^2$ (I)

where:

B is a backbone selected from the group consisting of:

Poly(ethylene glycol) (PEG):

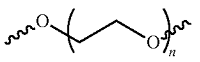

with n comprising between 1 to 450 repeating units,

Oligo(ethylene glycol) (EG):

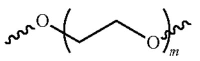

with m comprising between 1 to 12 repeating units,

Poloxamer:

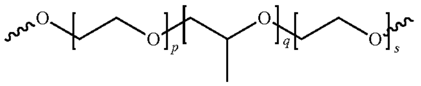

where p, q, s are independent from each other and comprise between 1 to 200 repeating units, Inverse Poloxamer:

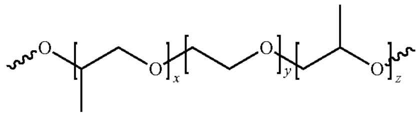

where x, y, z are independent from each other and comprise between 1 to 200 repeating units;

L is a linker selected among C3 to C18 linear or branched alkyl chains;

$R^1$ and $R^2$ are endgroups with $R^1$ being equal or different from $R^2$, where $R^1$ and $R^2$ are selected from the group consisting of: H, OH; acrylate;

methacrylate; acrylamide; methacrylamide; but-3-en-2-one; inverse methacrylate of formula

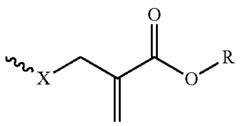

where R is an alkyl, X═O, NH; vinylsulfone; vinylurea; vinylcarbonate; vinylcarbamate; vinylthioester; vinylthiourea; with the proviso that $R^2$ is not H or OH when R1 is H or OH;

and with the proviso that when L=C3 then endgroups $R^1$ and $R^2$ are not acrylamide; or ii) a water soluble crosslinkable dental prepolymer for the preparation of chemically stable crosslinked polymer gels, said water soluble crosslinkable prepolymer having the formula II:

$R^1$-B-$R^2$ (II)

where:

B is a backbone consisting of:

Inverse Poloxamer:

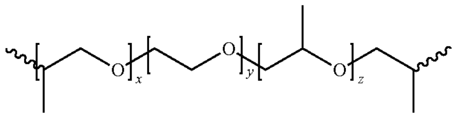

where x, y, z are independent from each other and comprise between 1 to 200 repeating units;

$R^1$ and $R^2$ are endgroups with R1 being equal or different from $R^2$, where $R^1$ and $R^2$ are selected from the group consisting of: H, OH; acrylate; methacrylate;

acrylamide; methacrylamide; but-3-en-2-one; inverse methacrylate of formula

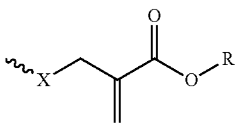

where R is an alkyl, X═O, NH; vinylsulfone; vinylurea; vinylcarbonate; vinylcarbamate; vinylthioester; vinylthiourea; with the proviso that $R^2$ is not H or OH when $R^1$ is H or OH, between 5-95% in weight of a suitable solvent, between 0.001-10% in weight of phenolic or aminoxyl radical stabilizers and between 0.001-10% in weight of a radical polymerization initiator.

7. The precursor composition according to claim 6, further comprising between 1-90% of inorganic fillers.

8. The precursor composition of claim 7, wherein the inorganic fillers are powders or suspensions and are selected from the group comprising non-water soluble metal oxides or salts.

9. A chemically stable crosslinked dental polymer gel composition obtainable by crosslinking the precursor composition according to claim 6, wherein said chemically stable crosslinked polymer gel composition retains at least 95% of its initial dry mass after being stored in water at 57° C. for 8 weeks and being subsequently subjected to a washing step and a vacuum drying step to remove any water or solvents.

10. A chemically stable crosslinked dental polymer gel composition obtainable by the process according to claim 1, wherein said chemically stable crosslinked polymer gel composition retains at least 95% of its initial dry mass after being stored in water at 57° C. for 8 weeks and being subsequently subjected to a washing step and a vacuum drying step to remove any water or solvents.

11. A medical or dental filler precursor composition comprising the precursor composition according to claim 6.

12. A water soluble crosslinkable dental prepolymer for the preparation of chemically stable crosslinked polymer gels, said water soluble crosslinkable prepolymer having the formula I:

$R^1$-L-B-L-$R^2$ (I)

where:

B is a backbone selected from the group consisting of:

Poly(ethylene glycol) (PEG):

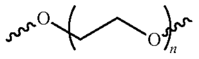

with n comprising between 1 to 450 repeating units,

Oligo(ethylene glycol) (EG):

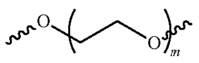

with m comprising between 1 to 12 repeating units,

Poloxamer:

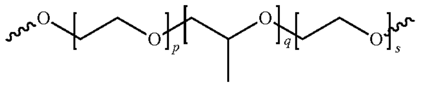

where p, q, s are independent from each other and comprise between 1 to 200 repeating units, Inverse Poloxamer:

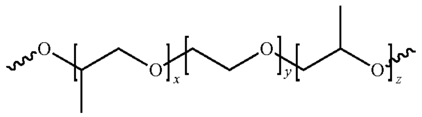

where x, y, z are independent from each other and comprise between 1 to 200 repeating units;

L is a linker selected among $C_3$ to $C_{18}$ linear or branched alkyl chains;

$R^1$ and $R^2$ are endgroups with $R^1$ being equal or different from R2, where $R^1$ and $R^2$ are selected from the group consisting of: H, OH; acrylate; methacrylate; but-3-en-2-one; inverse methacrylate of formula

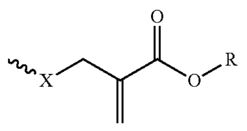

where R is an alkyl, X═O, NH; vinylsulfone; vinylurea; vinylcarbonate; vinylcarbamate; vinylthioester; vinylthiourea; with the proviso that $R^2$ is not H or OH when $R^1$ is H or OH;

with the proviso that when m=8, L is not C11.

13. The water soluble crosslinkable dental prepolymer according to claim 12, wherein $R^1$ and $R^2$ are selected from the group consisting of: acrylate and/or methacrylate.

14. The water soluble crosslinkable dental prepolymer according to claim 12, wherein the linker is a $C_4$ to $C_6$ linear or branched alkyl.

15. The process for preparing a chemically stable crosslinked polymer gel composition according to claim 1, wherein C3 is n-propyl or i-propyl.

16. The precursor composition of a chemically stable crosslinked dental polymer gel composition of claim 6, wherein C3 is n-propyl or i-propyl.

17. The water soluble crosslinkable dental prepolymer according to claim 12, wherein C11 is undecyl.

* * * * *